US010406363B2

(12) United States Patent
Sabesan

(10) Patent No.: US 10,406,363 B2
(45) Date of Patent: Sep. 10, 2019

(54) EVALUATION OF EFFICACY OF EPILEPSY THERAPY

(71) Applicant: LivaNova USA, Inc., Houston, TX (US)

(72) Inventor: Shivkumar Sabesan, Houston, TX (US)

(73) Assignee: LivaNova USA, Inc., Houston, TX (US)

(*) Notice: Subject to any disclaimer, the term of this patent is extended or adjusted under 35 U.S.C. 154(b) by 470 days.

(21) Appl. No.: 15/134,281

(22) Filed: Apr. 20, 2016

(65) Prior Publication Data

US 2016/0310070 A1  Oct. 27, 2016

Related U.S. Application Data

(60) Provisional application No. 62/150,773, filed on Apr. 21, 2015.

(51) Int. Cl.
*A61B 5/024* (2006.01)
*A61B 5/048* (2006.01)
*A61B 5/0402* (2006.01)
*A61N 1/36* (2006.01)
*A61B 5/00* (2006.01)

(52) U.S. Cl.
CPC .......... *A61N 1/36064* (2013.01); *A61B 5/024* (2013.01); *A61B 5/0402* (2013.01); *A61B 5/048* (2013.01); *A61B 5/4094* (2013.01); *A61B 5/4848* (2013.01); *A61B 5/686* (2013.01); *A61B 5/7285* (2013.01); *A61N 1/36053* (2013.01);
(Continued)

(58) Field of Classification Search
CPC ............ A61N 1/36064; A61N 1/36053; A61N 1/36135; A61B 5/024; A61B 5/0402; A61B 5/048; A61B 5/4094; A61B 5/4848; A61B 5/686; A61B 5/7285; A61B 5/7203; A61B 2562/0209
USPC .................................................. 600/544, 545
See application file for complete search history.

(56) References Cited

U.S. PATENT DOCUMENTS 6,016,449 A * 1/2000 Fischell ............... A61B 5/0476
607/45
6,061,593 A * 5/2000 Fischell ............... A61B 5/0476
600/544
(Continued)

FOREIGN PATENT DOCUMENTS

WO    WO-2009/043039    4/2009

OTHER PUBLICATIONS

International Search Report for PCT Patent Application No. PCT/US2016/028489, dated Jul. 28, 2016, 7 pages.
(Continued)

*Primary Examiner* — Navin Natnithithadha
(74) *Attorney, Agent, or Firm* — Foley & Lardner LLP

(57) ABSTRACT

A method of detecting an improvement in a seizure condition of a patient includes identifying a first EEG synchronization of the seizure condition of the patient; applying a therapy configured to improve the seizure condition of the patient; and identifying a second EEG synchronization of the seizure condition of the patient subsequent to application of the therapy, wherein an improvement of the seizure condition of the patient is demonstrated by a reduced EEG synchronization of the patient such that the second EEG synchronization is less than the first EEG synchronization.

31 Claims, 24 Drawing Sheets

(52) U.S. Cl.
CPC ..... *A61B 5/7203* (2013.01); *A61B 2562/0209* (2013.01); *A61N 1/36135* (2013.01)

(56) References Cited

U.S. PATENT DOCUMENTS

| | | | | |
|---|---|---|---|---|
| 6,128,538 | A * | 10/2000 | Fischell | A61B 5/0476 607/45 |
| 6,354,299 | B1 * | 3/2002 | Fischell | A61N 1/36025 128/899 |
| 6,360,122 | B1 * | 3/2002 | Fischell | A61B 5/0476 600/544 |
| 6,427,086 | B1 * | 7/2002 | Fischell | A61B 5/0476 607/45 |
| 6,459,936 | B2 * | 10/2002 | Fischell | A61N 1/36017 607/45 |
| 6,647,296 | B2 * | 11/2003 | Fischell | A61N 1/3605 600/544 |
| 8,560,073 | B2 * | 10/2013 | Osorio | A61B 5/0476 607/45 |
| 9,656,075 | B2 * | 5/2017 | Osorio | A61B 5/0476 |
| 2001/0051819 | A1 * | 12/2001 | Fischell | A61N 1/3605 607/45 |
| 2001/0056290 | A1 * | 12/2001 | Fischell | A61N 1/36017 607/45 |
| 2002/0002390 | A1 * | 1/2002 | Fischell | A61B 5/0476 607/45 |
| 2002/0099412 | A1 * | 7/2002 | Fischell | A61N 1/36025 607/3 |
| 2010/0286747 | A1 * | 11/2010 | Sabesan | A61B 5/0476 607/45 |
| 2011/0160795 | A1 * | 6/2011 | Osorio | A61B 5/0476 607/45 |
| 2011/0295332 | A1 | 12/2011 | Osorio | |
| 2013/0096839 | A1 | 4/2013 | Osorio et al. | |
| 2014/0052213 | A1 * | 2/2014 | Osorio | A61B 5/0476 607/45 |

OTHER PUBLICATIONS

Shunan et al., A Novel Feature Extraction Method for Epilepsy EEG Signals Based on Robust Generalized Synchrony Analysis, Control and Decision Conference (CDCC), 2013 25th Chinese, IEEE, May 25, 2013, 4 pages.

Fraschini, et al., VNS induced desynchronization in gamma bands correlates with positive clinical outcome in temporal lobe pharmacoresistant epilepsy, Neuroscience Letters, vol. 536, Mar. 1, 2013, 5 pages.

Hammond, et al., Electrophysiological studies of cervical vagus nerve stimulation in humans: I. EEG effects, Epilepsia, vol. 33, No. 6, Nov.-Dec. 1992, 8 pages.

Koo, B., EEG changes with vagus nerve stimulation, Journal of Clinical Neurophysiology, vol. 18, No. 5, Sep. 2001, 8 pages.

Kuba, et al., Effect of vagal nerve stimulation on interictal epileptiform discharges: a scalp EEG study, Epilepsia, vol. 43, No. 10, Oct. 2002, 8 pages.

Marrosu, et al., Increase in 20-50 Hz (gamma frequencies) power spectrum and synchronization after chronic vagal nerve stimulation, Clinical Neurophysiology, vol. 116, No. 9, Sep. 2005, 11 pages.

Vos, et al., Predicting success of vagus nerve stimulation (VNS) from interictal EEG, Seizure, vol. 20, No. 7, Sep. 2011, 5 pages.

* cited by examiner

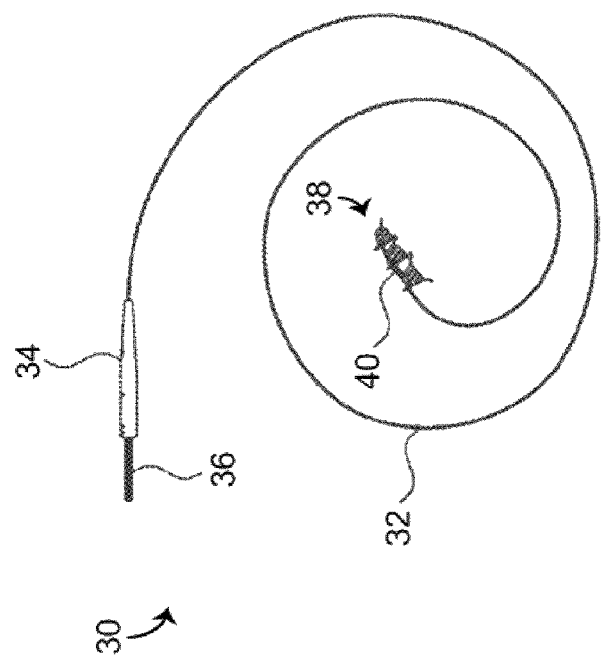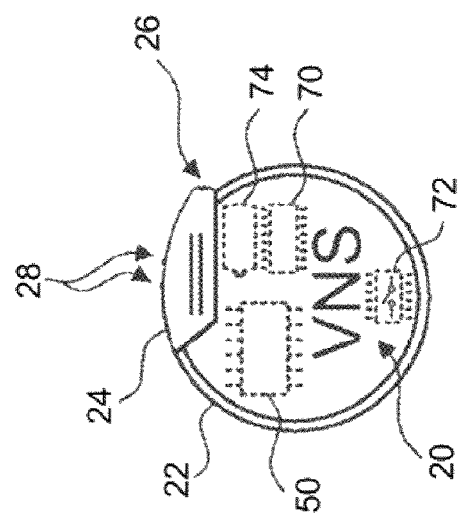
FIG. 1

| Subject | Sex | Age | Previous Brain or Epilepsy Surgery | 4 or more AED | EMU duration days | # of pre-treatment Seizures | # of post-treatment Seizures |
|---|---|---|---|---|---|---|---|
| 1 | M | 21 | N | Y | 3 | 6 | 3 |
| 2 | F | 31 | Y | Y | 3 | 10 | 11 |
| 3 | M | 25 | N | Y | 4 |  | 3 |
| 4 | M | 23 | Y | Y | 4 | 4 | 4 |
| 5 | F | 27 | Y | Y | 3 |  | 1 |
| 6 | M | 48 | N | Y | 4 | 7 | 17 |
| 7 | F | 28 | Y | Y | 9 | 10 | 1 |
| 8 | M | 34 | Y | N | 4 | 3 |  |
| 9 | M | 24 | Y | Y | 4 | 1 | 1 |
| 10 | F | 61 | Y | Y | 4 |  | 1 |
| 11 | F | 69 | N | Y | 4 |  | 1 |
| 12 | F | 29 | N | Y | 4 |  | 2 |
| 13 | F | 38 | N | Y | 4 | 2 | 1 |
| 14 | F | 50 | N | Y | 4 |  | 1 |
| 15 | F | 41 | N | Y | 4 | 1 |  |
| 16 | F | 24 | N | Y | 4 | 40 | 7 |
| 17 | F | 21 | Y | N | 4 | 6 | 10 |
| 18 | M | 32 | N | Y | 4 | 2 |  |
| 19 | F | 30 | N | Y | 4 |  | 4 |
| 20 | F | 39 | Y | Y | 4 | 3 | 1 |
| 21 | F | 26 | Y | Y | 3 |  | 8 |
| 22 | F | 22 | Y | Y | 4 |  | 3 |
| 23 | F | 61 | N | Y | 3 | 1 |  |
| 24 | F | 37 | N | Y | 4 | 1 | 1 |
| 25 | F | 47 | Y | Y | 4 | 2 |  |
| 26 | F | 62 | N | Y | 5 |  | 6 |
| 27 | M | 22 | N | N | 3 | 2 | 5 |
| 28 | M | 36 | N | Y | 4 |  | 1 |
| 29 | F | 47 | N | Y | 4 | 2 | 3 |
| 30 | F | 26 | N | Y | 4 |  | 8 |
| 31 | M | 52 | N | Y | 4 |  | 4 |
| 32 | M | 51 | N | Y | 4 | 1 |  |
| 33 | M | 28 | N | Y | 4 | 1 |  |
| 34 | F | 41 | N | Y | 4 | 8 |  |
| 35 | F | 38 | Y | Y | 3 | 1 | 40 |
| 36 | M | 50 | N | Y | 3 | 2 | 1 |
| 37 | F | 44 | N | Y | 4 | 8 | 1 |
| 38 | F | 57 | N | Y | 4 |  | 6 |

FIG. 13

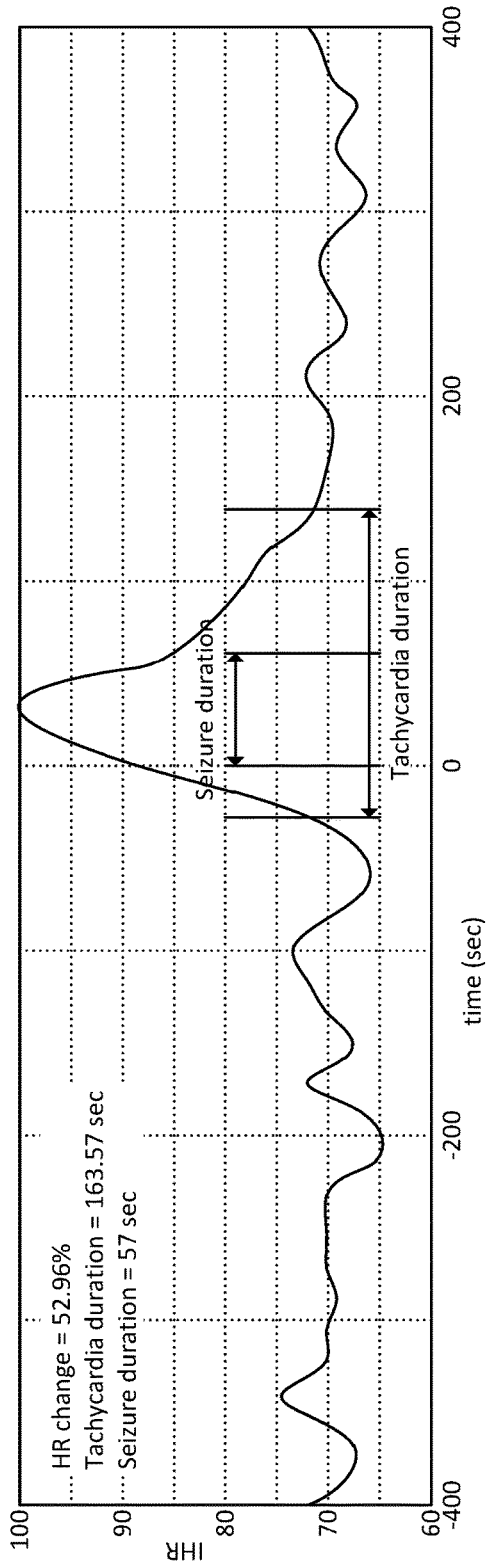
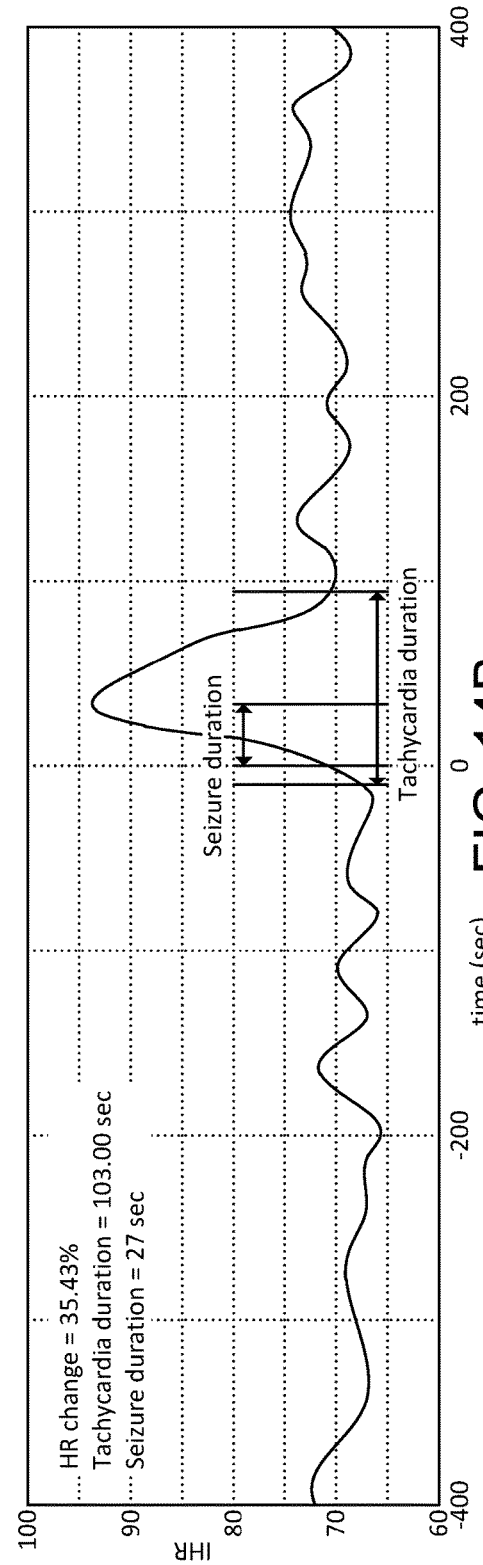

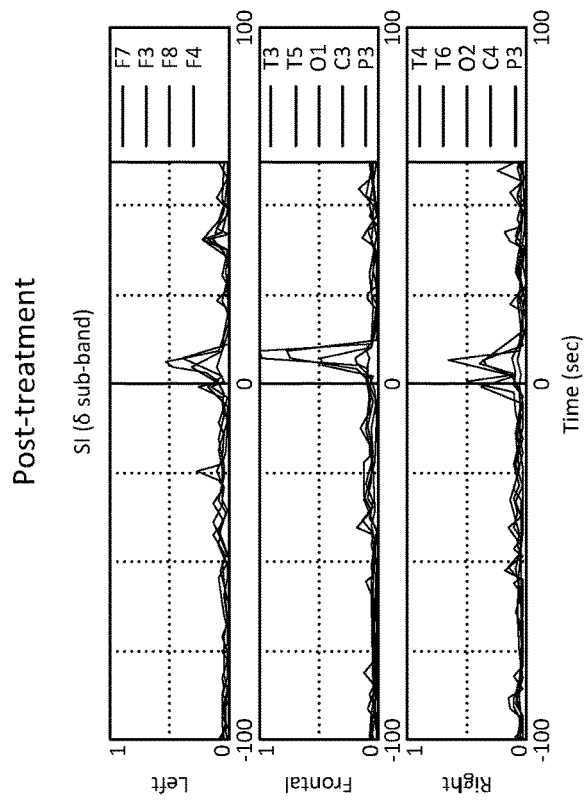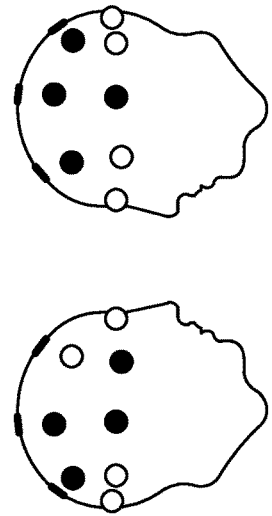
FIG. 16B
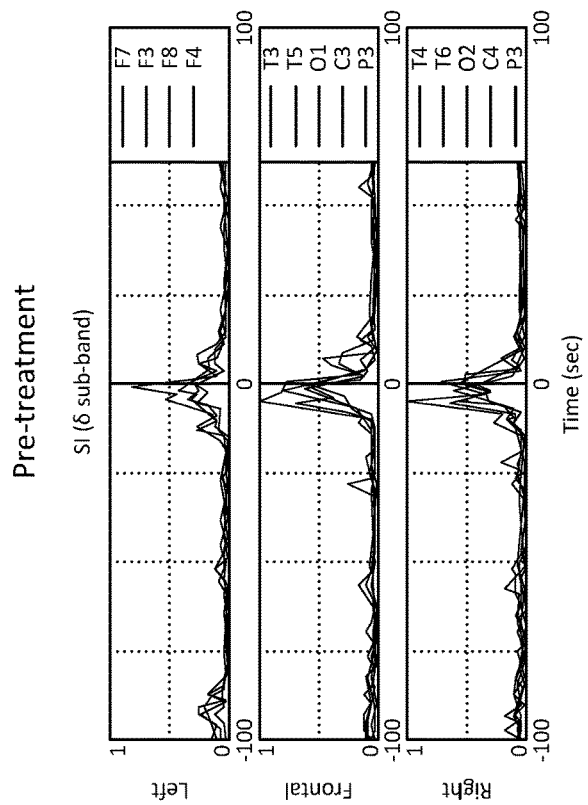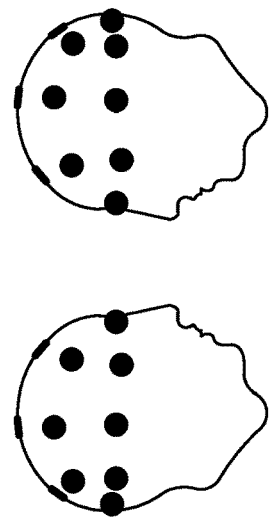
FIG. 16A

| Feature # | Feature | Average(±Std) for pre-treatment | Average(±Std) for post-treatment | t-statistic values | p-values |
|---|---|---|---|---|---|
| 1 | HR change (beats per minute) | 64.5548±27.38 | 28.55±28.87 | 10.60 | 2.84e-22 |
| 2 | Tachycardia duration (sec) | 162.42±105.76 | 88.40±72.07 | 6.95 | 2.67e-11 |
| 3 | % of synchronized EEG electrodes | 90.91±18.12 | 23.27±35.34 | 19.37 | 1.59e-53 |

FIG. 18A

| Classes | Predicted Pre-treatment | Predicted Post-treatment | % correct | Total performance |
|---|---|---|---|---|
| Pre-treatment | 99 | 25 | 79.84% | 83.57% |
| Post-treatment | 21 | 135 | 86.54% | |

FIG. 18B

| Classes | Pre-treatment | Post-treatment | % correct | Total performance |
|---|---|---|---|---|
| Pre-treatment | 106 | 18 | 85.48% | 79.90% |
| Post-treatment | 21 | 49 | 70.00% | |

FIG. 18C

EVALUATION OF EFFICACY OF EPILEPSY THERAPY

CROSS-REFERENCE TO RELATED PATENT APPLICATIONS

This application claims priority to and the benefit of U.S. Provisional Application No. 62/150,773, filed Apr. 21, 2015, which is hereby incorporated by reference herein in its entirety.

BACKGROUND

The present disclosure relates generally to the field of therapy for a reduction in severity of seizures in patients.

Approximately 3 million people in the US have epilepsy, of whom 10% to 20% have a form of epilepsy that is not well controlled with anti-epileptic drugs (i.e. drug refractory). Patients with drug refractory epilepsy may seek alternative solutions such as surgical resection, ketogenic diet and neuromodulation. Vagus nerve stimulation, or VNS Therapy®, is an FDA approved neuromodulation treatment that may be used as an adjunctive therapy to pharmacology and has been demonstrated to reduce seizure frequency in a multicenter, randomized controlled trial as well as in subsequent single center trials. A current, commercially available VNS Therapy utilizes an open loop stimulation paradigm (i.e. the stimulation is delivered using a predetermined duty cycle (i.e. "ON" and "OFF" times)) with parameters that are physician programmable (i.e. current amplitude, pulse width, frequency). In addition, VNS Therapy provides patients and caregivers with an opportunity to administer stimulation on demand during or just prior to a seizure via the use of a portable magnet. The use of such a magnet to manually activate on-demand stimulation has been reported to terminate or in some cases, reduce the severity of seizures. However, not all patients have the ability to apply the magnet before the onset of a seizure and/or experience an aura (i.e., an early warning of an impending clinical seizure).

SUMMARY

One embodiment relates to a method of detecting an improvement in a seizure condition of a patient. The method includes identifying a first EEG synchronization of the seizure condition of the patient; applying a therapy configured to improve the seizure condition of the patient; and identifying a second EEG synchronization of the seizure condition of the patient subsequent to application of the therapy, wherein an improvement of the seizure condition of the patient is demonstrated by a reduced EEG synchronization of the patient such that the second EEG synchronization is less than the first EEG synchronization.

Another embodiment relates to a device configured to detect an improvement in a seizure condition of a patient. The device includes at least one EEG sensor configured to generate EEG data and a therapy analysis device configured to receive the EEG data. The therapy analysis device is configured to evaluate an effect of a therapy. The evaluation includes identifying a first EEG synchronization of the seizure condition of the patient, applying a therapy configured to improve the seizure condition of the patient, and identifying a second EEG synchronization of the seizure condition of the patient subsequent to application of the therapy, wherein an improvement of the seizure condition of the patient is demonstrated by a reduced EEG synchronization of the patient such that the second EEG synchronization is less than the first EEG synchronization.

Yet another embodiment relates to a method of detecting an improvement in a seizure condition of a patient. The method includes identifying a first EEG synchronization of the seizure condition of the patient by extracting first maximum wavelet coefficients in a first plurality of epochs and a plurality of frequency bands for a plurality of EEG sensors; computing a first global spatial synchronization for each frequency band across the plurality of EEG sensors using the first maximum wavelet coefficients; and estimating a first synchronizability index for each of the plurality of EEG sensors using the first global spatial synchronization. The method further includes applying stimulation to a vagus nerve of the patient using a vagus nerve stimulation device configured to improve the seizure condition of the patient. The method further includes identifying a second EEG synchronization of the seizure condition of the patient subsequent to application of the stimulation by extracting second maximum wavelet coefficients in a second plurality of epochs and the plurality of frequency bands for the plurality of EEG sensors; computing a second global spatial synchronization for each frequency band across the plurality of EEG sensors using the second maximum wavelet coefficients; and estimating a second synchronizability index for each of the plurality of EEG sensors using the second global spatial synchronization. The method further includes generating an indication of an efficacy of the stimulation to the vagus nerve using at least one of the second synchronizability index or a comparison of the second synchronizability index to the first synchronizability index.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Further features, characteristics and advantages of the present disclosure will become apparent to a person of ordinary skill in the art from the following detailed description of embodiments of the present disclosure, made with reference to the drawings annexed, in which like reference characters refer to like elements, and in which:

FIG. 1 is an illustration of a nerve stimulation device having a neurostimulator and a lead, according to an example embodiment;

FIG. 13 is a table showing a summary of patients' characteristics;

FIG. 14A is a graph displaying a magnitude and duration of a heart rate increase during a seizure before VNS therapy, according to an example embodiment;

FIG. 14B is a graph displaying a magnitude and duration of a heart rate increase during a seizure after VNS therapy, according to an example embodiment;

FIG. 16A is the synchronizability index for the δ frequency sub-band showing the synchronized electrodes during a seizure before VNS therapy, according to an example embodiment;

FIG. 16B is the synchronizability index for the δ frequency sub-band showing the synchronized electrodes during a seizure after VNS therapy, according to an example embodiment;

FIG. 18A is a table showing the statistical data as a result of the study performed;

FIG. 18B is a table showing the classification performance in predicting seizures according to the results of the study; and FIG. 18C is a table showing the classification of seizures that received VNS therapy according to the results of the study.

DETAILED DESCRIPTION

Figure 2:
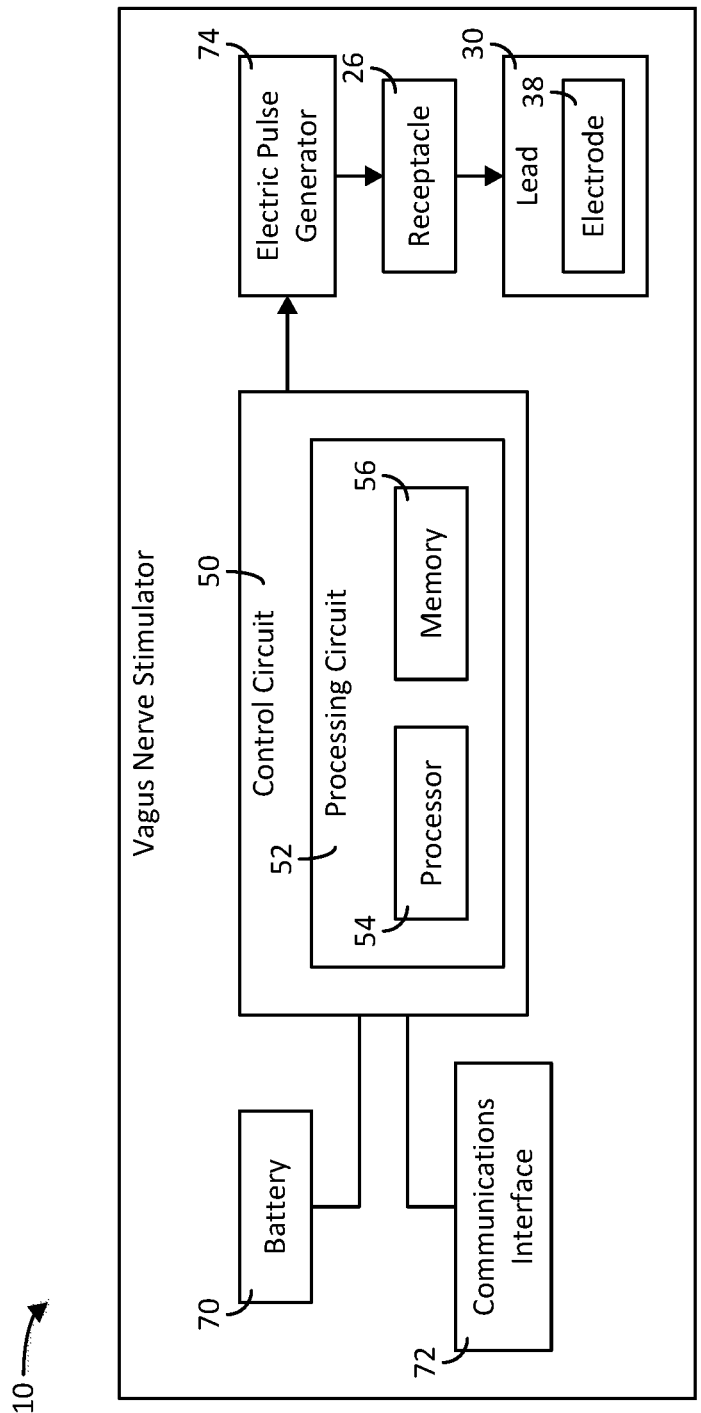
FIG. 2 is schematic block diagram of the nerve stimulation device of FIG. 1, according to an example embodiment.

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection is defined by the claims that follow this description and not by any particular embodiment described herein. Before turning to the figures, which illustrate example embodiments in detail, it should be understood that the application is not limited to the details or methodology set forth in the description or illustrated in the figures. It should also be understood that the terminology is for the purpose of description only and should not be regarded as limiting.

The Cyberonics AspireSR™ neurostimulator incorporates a closed-loop system that detects potential seizure events associated with heart rate increase and automates the magnet activation and thereby delivers stimulation automatically. This feature of the device is called the automated magnet mode (AMM) feature and represents one computationally efficient means of achieving closed-loop neuromodulation. The seizure detection algorithm within AspireSR leverages that seizure origination and/or propagation may functionally impair neural circuits involved in sympathetic cardiovascular regulation in the mesial temporal lobe structures that can manifest as tachycardia during a seizure (ictal state).

Recently, a prospective, multi-center clinical trial in an epilepsy monitoring unit (EMU) environment was conducted where the detection performance of this algorithm was tested against the visual inspection of EEG. This clinical trial (NCT01325623) met its primary endpoint of achieving greater than 80% sensitivity in seizure detection.

The clinical benefit of open-loop VNS have been shown in several studies. One metric of assessing clinical benefit of VNS or any other therapy in epilepsy has been seizure frequency reduction as measured using seizure diaries. However, as discussed above, these diaries have been shown to be inaccurate and subjective. In addition, several qualitative scales that assess quality of life and severity of the seizure disorder have been suggested; however, they are seldom used in clinical practice or in clinical studies as a primary endpoint for evaluating new therapies for epilepsy. This has motivated the need to identify reliable and measurable biomarkers of efficacy of epilepsy therapy in general, and VNS in particular. A few researchers have examined the effects of VNS using objective measures of EEG (electroencephalographic) activity.

A study in this area by Hammond et al., titled "Electrophysiological studies of cervical vagus nerve stimulation in humans: I. EEG effects" proved that VNS may interrupt ongoing ictal EEG activity. Then, Koo et al. revealed progressive decrease in duration and frequency of spikes and wave activity on interracial EEG signals by long term monitoring the effects of chronic VNS in "EEG changes with vagus nerve stimulation." Kuba et al. showed that acute stimulation of vagal nerves reduces the number of interictal epileptiform discharges where the reduction is most prominent during the stimulation periods in "Effect of vagal nerve stimulation on interictal epileptiform discharges: a scalp EEG study." Marrosu et al. have used EEG frequency profile in a study to determine the effect of chronic VNS therapy, as described in "Increase in 20-50 Hz (gamma frequencies) power spectrum and synchronization after chronic vagal nerve stimulation." Marrosu et al. evaluated the power spectrum density and synchronization from EEGs before and after VNS therapy and identified decreases in the synchronization in theta band and increases in power spectrum and synchronization in gamma (20-50 Hz) after VNS therapy.

Later in another study by Fraschini et al., titled "VNS induced desynchronization in gamma bands correlates with positive clinical outcome in temporal lobe pharmacoresistant epilepsy," used phase lag index to compare the EEG synchronization in responders and non-responders to chronic VNS therapy. Fraschini et al. found a statistical decrease in de-synchronization in gamma band after five years from VNS surgery, in responders to the VNS therapy, while the other frequency bands do not show significant variation. Vos et al. used a pair wise derived brain symmetry index (pdBSI) to indicate a possibility of predicting a response to VNS therapy from interictal EEG before the onset of VNS therapy, as described in "Predicting success of vagus nerve stimulation (VNS) from interictal EEG." Vos et al. realized, on average, lower pdBSI values in responders than non-responders in all four frequency sub-bands of $\delta$, $\theta$, $\alpha$, and $\beta$, where the average pdBSI is significantly discriminating between responders and non-responders in the two frequency sub-bands of $\theta$ and $\alpha$. Vos et al. concluded that pdBSI could be used as a feature to predict the response to VNS therapy as the responders have, on average, less asymmetric spectral characteristics of the interictal EEG than non-responders.

Vagus nerve stimulation (VNS) therapy is an adjunctive therapy for patients with medically refractory epilepsy. One of the primary metrics used to assess a response to any treatment for epilepsy is seizure frequency reduction. This is generally measured using subjective patient-reported outcomes, such as seizure diaries. However, it has been shown that self-reporting of seizure frequency is severely inaccurate. In addition to seizure frequency, reduction in seizure severity is clinically meaningful to patients and can be measured objectively. Analysis of electro-encephalographic (EEG) and electro-cardiographic (ECG/EKG) signals have revealed that seizures are accompanied by spatial synchronization of EEG and increased heart rates that may persist for several minutes to hours after the seizure, increasing the likelihood of Sudden Unexplained Death in Epilepsy (SUDEP). In view of this understanding, it may be possible to show that the automated delivery of VNS at a time of seizure onset (i.e. closed-loop) reduces a severity of seizures in patients with epilepsy by showing a reduction in EEG spatial synchronization as well as a reduction in the duration and magnitude of an accompanying heart rate increase.

From a cardiovascular perspective, ictal discharges that occur in or propagate to key brain structures that regulate autonomic function can lead to increased sympathetic outflows, impacting autonomic function. This increased sympathetic tone to the heart has been measured using heart rate variability (HRV) analysis. HRV markers of sympathetic tone dominance have been shown to be strong and independent predictors of mortality including sudden cardiac death in patients after an acute myocardial infarction as well as in those with heart failure or cardiomyopathy. This also implies that a therapy that is effective may alter HRV. Recently, reduction in T-wave alternans (TWA) has been shown to be an indicator of VNS therapy in patients with epilepsy. However, the signal-to-noise ratio for T-wave measurements is significantly lower than R-wave and is more prone to variations due to body position/location than R-waves. This makes TWA a difficult marker to monitor chronically to study the effects of VNS. It has been shown that generalized seizures appear to have higher heart rate increases that last for a longer time than complex partial seizures, suggesting that another metric of evaluating the effectiveness of a therapy may be to study its effect in reducing ictal tachycardia increase and duration. Moreover, from a signal processing perspective, measuring heart rate (via R-wave detection) is significantly easier than other morphological parameters of ECG.

According to some embodiments of the present disclosure, the performance of the AMM feature in reducing the severity of seizures in patients with epilepsy can be evaluated by using a combination of features obtained from continuous observational video electroencephalography (vEEG) and electrocardiogram (ECG) data around ictal events. These events may occur during a epilepsy monitoring unit (EMU) evaluation (e.g., 3 to 5 days). Performance of the AMM feature may be measured by the ability to discriminate (classify) seizures in patients prior to using VNS therapy from the ones that occur following AMM-based VNS therapy. In order to achieve this, in some embodiments, three features may be utilized 1) heart rate amount (e.g., percentage, peak heart rate increase) change during tachycardia, 2) tachycardia duration (e.g., in seconds) and 3) number of EEG electrodes that contribute the most to a global spatial synchronization that accompany seizures, to show that application of AMM-based VNS therapy reduces the ictal spatial synchronization (as measured by EEG-based features) and the autonomic effects of seizures (as measured by ECG-based features).

Referring to the Figures generally, the present disclosure relates to apparatuses, systems, and methods for verifying the efficacy of VNS therapy to reduce the severity of seizures for patients. Seizures are caused by problems in electrical signaling of the brain. Individuals who suffer from reoccurring seizures are generally diagnosed with epilepsy. Seizures may affect a specific area of the brain (e.g., the left hemisphere) or may be more widespread in the brain and affect a larger area. With VNS, the electrical energy that is discharged disrupts the abnormal brain activity, which may decrease seizure activity and therefore severity.

Therefore, VNS may be used for the treatment of seizures. During VNS, stimulation may be directly and/or indirectly applied to the vagus nerve with a lead having an electrode powered by an implantable neurostimulator. By way of example, the electrode (e.g., a cuff-type electrode, a helical-type electrode, etc.) may be attached to the exterior of the vagus nerve (e.g., at the cervical level of the vagus nerve, etc.) to provide VNS directly to the vagus nerve.

However, VNS may not reduce the severity of seizures for some patients. In fact, in some instances, VNS may adversely affect some patients (e.g., leading to worse health issues, high medical costs for ineffective medical procedures, etc.). Thus, VNS can be evaluated to determine if the therapy is effective in reducing the severity of seizures. By determining the effectiveness of the therapy, a physician may alter parameters of the VNS to obtain a higher efficacy of treatment.

According to an exemplary embodiment, the apparatuses, systems, and methods of the present disclosure are used to determine the efficacy of applying VNS to patients that have reoccurring seizures. In some embodiments, this may be done by analyzing a percent of heart rate change during a seizure, a duration of heart rate change during a seizure, and/or a measure of spatial synchronization of EEG during a seizure. These measurements may be used separately or in conjunction with one another to determine efficacy or severity of a seizure. This information can be compared for an individual before and after receiving automatic VNS. Such a determination may lead to reduced severity of seizures for patients, as well as provide physicians with information relating to parts of the brain that are still being affected by the seizure.

Figure 3:
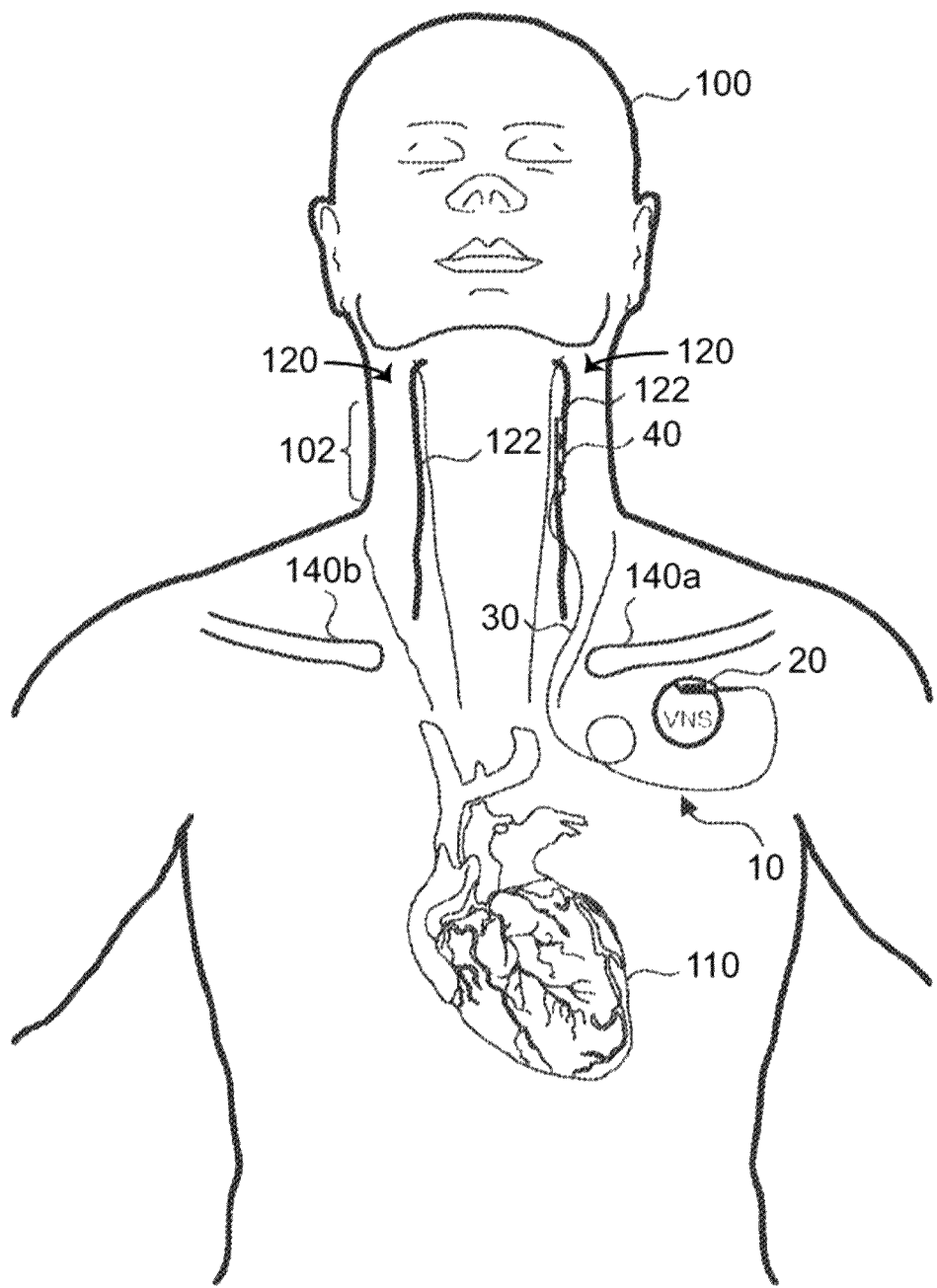
FIG. 3 is an illustration of the nerve stimulation device of FIG. 1 implanted within a patient to provide vagus nerve stimulation, according to an example embodiment.

Referring now to FIGS. 1-3, an implantable stimulation device, shown as vagus nerve stimulator 10, may be implanted within a person, shown as patient 100, to provide VNS.

However, other forms of neuromodulation may be used as well and are intended to fall within the spirit and scope of the present disclosure. Additionally, the efficacy evaluation techniques presented in the present disclosure are equally applicable to other forms of epilepsy therapy as well, such as drug-based therapies. Thus, while various embodiments herein are discussed with respect to neuromodulation therapy such as VNS, the techniques discussed herein are contemplated for use with any epilepsy therapy, and use of the techniques with all such therapies is within the scope of the present disclosure. Such a vagus nerve stimulator 10 may be adapted for use in managing severity of seizures through therapeutic vagal stimulation. According to an exemplary embodiment, the vagus nerve stimulator 10 operates under several mechanisms of action. These mechanisms may include disrupting abnormal brain activity through stimulation. More importantly, the stimulation provided by the vagus nerve stimulator 10 may be triggered by an automated magnet mode (AMM) that detects potential seizure events, which may be associated with heart rate increase, and automates a magnet activation and thereby delivers stimulation automatically.

As shown in FIGS. 1-2, the vagus nerve stimulator 10 includes an implantable neurostimulator, shown as neurostimulator 20 and a therapy lead, shown as lead 30. According to an exemplary embodiment, the neurostimulator 20 is configured to generate an electrical signal that the lead 30 delivers to a desired location (e.g., the vagus nerve, etc.). As shown in FIG. 1, the neurostimulator 20 includes a housing, shown as hermetically sealed housing 22. According to an exemplary embodiment, the hermetically sealed housing 22 is manufactured from a biocompatible, implantation-safe material (e.g., titanium, etc.). The neurostimulator 20 includes a connector cover, shown as header 24, coupled to the hermetically sealed housing 22. The header 24 is portioned to enclose a connection interface, shown as receptacle 26. While vagus nerve stimulation 10 is illustrated as an implantable neurostimulator, in other embodiments, a non-implantable or external neurostimulation device could be used.

The lead 30 includes a wire, shown as lead wire 32. In one embodiment, the lead wire 32 includes a silicone-insulated alloy conductor material. The lead 30 includes a connector, shown as a lead connector 34, positioned on a proximal end of the lead wire 32. As shown in FIG. 1, the lead connector 34 transitions from an insulated electrical lead body to a connection interface, shown as connector pin 36 (e.g., a metal connector pin, etc.). In one embodiment, the lead connector 34 is manufactured using silicone and the connector pin 36 is made of stainless steel, although other suitable materials may be used as well. According to an exemplary embodiment, the connector pin 36 is configured to be received by the receptacle 26 of the neurostimulator 20 to couple the lead 30 thereto. During implantation, the connector pin 36 is guided through the receptacle 26 into the header 24 and securely fastened in place using a fastener, shown as set screws 28, thereby electrically coupling the lead 30 to the neurostimulator 20. In one embodiment, the header 24 encloses the receptacle 26 into which a single connector pin 36 for the lead 30 may be received. In other embodiments, two or more receptacles 26 may also be provided, to couple additional leads 30 to the neurostimulator 20.

As shown in FIGS. 1-2, the lead 30 includes a simulation element, shown as electrode 38. As shown in FIG. 1, the electrode 38 is positioned on a distal end of the lead wire 32. According to the exemplary embodiment shown in FIG. 1, the electrode 38 includes a cuff-type electrode 40. In other embodiments, the electrode 38 includes another type of electrode (e.g., a pig-tail or helical electrode, etc.). In some embodiments, another type of lead is used (e.g., a stent, a pig-tail lead, a preformed lead, etc.). According to an exemplary embodiment, the electrode 38 is configured to deliver an electrical signal from the neurostimulator 20 to a desired location (e.g., the vagus nerve, etc.).

As shown in FIGS. 1-2, the neurostimulator 20 includes (e.g., contained within the hermetically sealed housing 22, etc.) electronic circuitry, shown as control circuit 50, an energy storage device, shown as battery 70, a communications interface, shown as communications interface 72, and a pulse generator, shown as electric pulse generator 74. The battery 70 is configured to power the neurostimulator 20 (e.g., the control circuit 50, the electric pulse generator 74, the communications interface 72, etc.). In some embodiments, the battery 70 includes a lithium carbon monoflouride battery. In other embodiments, the battery 70 includes another type of battery (e.g., a lithium-ion battery, a nickel-metal hydride battery, etc.). According to an exemplary embodiment, the communications interface 72 is configured to provide remote access to the operation of the neurostimulator 20 using an external programmer, a simple patient magnet, and/or an electromagnetic controller. In one embodiment, the communications interface 72 includes a Reed circuit. In some embodiments, the communications interface 72 includes a transceiver that remotely communicates with the external programmer using a wireless communication protocol (e.g., radio frequency signals, Bluetooth, etc.) to receive programming instructions and/or transmit telemetry information to the external programmer or other external device. In some embodiments, other components, such as an integrated heart rate sensor, may be integrated within the neurostimulator 20.

According to an exemplary embodiment, the control circuit 50 is configured to control the electric pulse generator 74 to generate electric pulses to be delivered by the lead 30 (e.g., the electrode 38, etc.) to provide stimulation to a desired location (e.g., the vagus nerve, etc.). Thereby, the neurostimulator 20 may deliver VNS under control of the control circuit 50 based on stored stimulation parameters that are programmable (e.g., by a physician, by the manufacturer, etc.). Each stimulation parameter may be independently programmed to define the characteristics of the cycles of therapeutic stimulation and inhibition to ensure optimal stimulation for a patient. The programmable stimulation parameters may include output current, signal frequency, pulse width, signal ON time, signal OFF time, magnet activation (e.g., for VNS specifically triggered by magnet mode, etc.), and/or reset parameters. Other programmable parameters are possible. In addition, sets or "profiles" of preselected stimulation parameters may be provided to physicians with the external programmer and fine-tuned to a patient's physiological requirements prior to being programmed into the neurostimulator 20.

The neurostimulator 20 may be interrogated prior to implantation and throughout the therapeutic period with a healthcare provider-operable external programmer and programming wand for checking proper operation, downloading recorded data, diagnosing problems, and programming operational parameters. In some embodiments, use of the external programmer is restricted to healthcare providers, while more limited manual control is provided to the patient through magnet mode. In one embodiment, the external programmer executes application software specially designed to interrogate the neurostimulator 20. The programming computer may interface to the programming wand through a standardized or proprietary wired or wireless data connection. Other configurations and combinations of external programmer, programming wand, and/or application software are possible.

As shown in FIG. 2, the control circuit 50 of the vagus nerve stimulator 10 includes a processing circuit 52. The processing circuit 52 includes a processor 54 and a memory 56. The processor 54 may be implemented as a general-purpose processor, an application specific integrated circuit (ASIC), one or more field programmable gate arrays (FPGAs), a digital signal processor (DSP), a group of processing components, or other suitable electronic processing components. The memory 56 (e.g., RAM, ROM, Flash Memory, etc.) may store data and/or computer code for facilitating the various processes described herein. Thus, the memory 56 may be communicably connected to the processor 54 and provide computer code or instructions to the processor 54 for executing the processes described in regard to the vagus nerve stimulator 10 herein. Moreover, the memory 56 may be or include tangible, non-transient volatile memory or non-volatile memory. In some embodiments, the memory 56 may include database components, object code components, script components, or any other type of information structure for supporting the various activities and information structures described herein.

The memory 56 may include various circuits for completing processes described herein. More particularly, the memory 56 includes circuits configured to control operation of the vagus nerve stimulator 10 to provide VNS. The memory 56 may store instructions that operate the vagus nerve stimulator 10 according to stored stimulation parameters and timing cycles (e.g., a predefined stimulation protocol, automated magnet mode, etc.). For example, the memory 56 may include a voltage regulator that regulates system power, a stimulation manager that controls the overall pulse generator function, an input circuit that receives and implements programming commands from the external programmer or other external source, and/or data storage that collects and stores telemetry information, among other possible circuits that perform additional or alternative functions. While various circuits with particular functionality may be used, it will be understood that the memory 56 may include any number of circuits for completing the functions described herein. For example, the activities of multiple circuits may be combined as a single circuit; additional circuits with additional functionality may be included. Further, it will be understood that the processing circuit 52 of the vagus nerve stimulator 10 may further control other processes beyond the scope of the present disclosure.

According to the exemplary embodiment shown in FIG. 3, the neurostimulator 20 is implanted into the right or left pectoral region of a patient 100. Generally, the neurostimulator 20 is implanted on the same side (ipsilateral) of the patient's body as the vagus nerve 120 to be stimulated (e.g., right or left vagus nerve 120, etc.), although other neurostimulator-vagus nerve configurations, including contra-lateral and bi-lateral, are possible. As shown in FIG. 3, the cuff-type electrode 40 is implanted on the main trunk 122 of the vagus nerve 120 about halfway between the clavicle 140a-b and the mastoid process (e.g., at the cervical level, etc.). The lead 30 and cuff-type electrodes 40 may be implanted by first exposing the carotid sheath and chosen vagus nerve 120 through a latero-cervical incision on the ipsilateral side of the neck 102 of the patient 100. The cuff-type electrodes 40 are then placed onto the exposed nerve sheath and tethered. A subcutaneous tunnel is formed between the respective implantation site of the neurostimulator 20 and cuff-type electrode 40, through which the lead 30 is guided to the neurostimulator 20 and securely connected. Such an implantation requires an invasive surgical procedure under general anesthesia.

Once implantation of the vagus nerve stimulator 10 is completed, the neurostimulator 20 may provide VNS directly to the main truck 122 of the vagus nerve 120 with the cuff-type electrode 40. The stimulation produces action potentials in the underlying nerves that propagate bi-directionally, in some embodiments. Both sympathetic and parasympathetic nerve fibers may be stimulated through the cuff-type electrode 40 of the vagus nerve stimulator 10. Stimulation of the cervical vagus nerve 120 results in propagation of action potentials in both afferent and efferent directions from the site of stimulation to restore autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 110 to activate the components of the heart's intrinsic nervous system. Either the left or right vagus nerve 120 may be stimulated by the vagus nerve stimulator 10, although stimulation of the right vagus nerve 120 has a moderately stronger effect on heart rate (e.g., on the order of approximately 20% stronger) than left vagus nerve 120 stimulation at the same parametric levels.

At the cervical level, the vagus nerve 120 contains afferent fibers but also efferent ones innervating most of the intra-thoracic and abdominal organs as well as the laryngeal area through the recurrent laryngeal nerve which is included with the vagus nerve 120 in the neck 102. Stimulating the vagus nerve 120 in the cervical region may lead to adverse effects, related to large innervated areas, including cough, voice alteration/hoarseness, pain, dyspnea, nausea, etc.

Figure 4B:
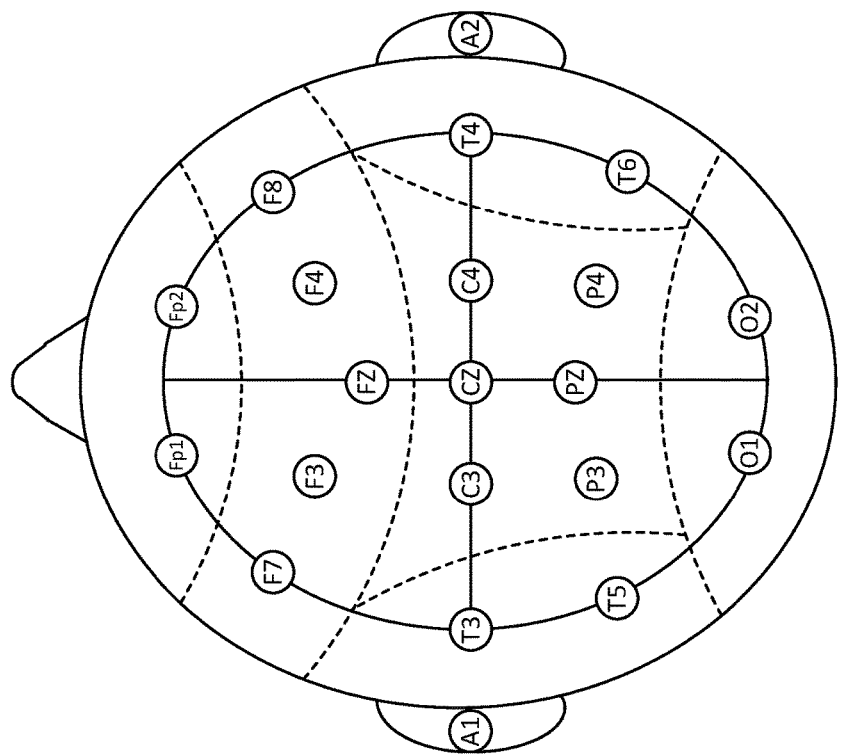
FIGS. 4A-4B are diagrams showing electrode placement for collecting EEG signals with a left side view and a top view, respectively, according to an example embodiment.
Figure 4A:
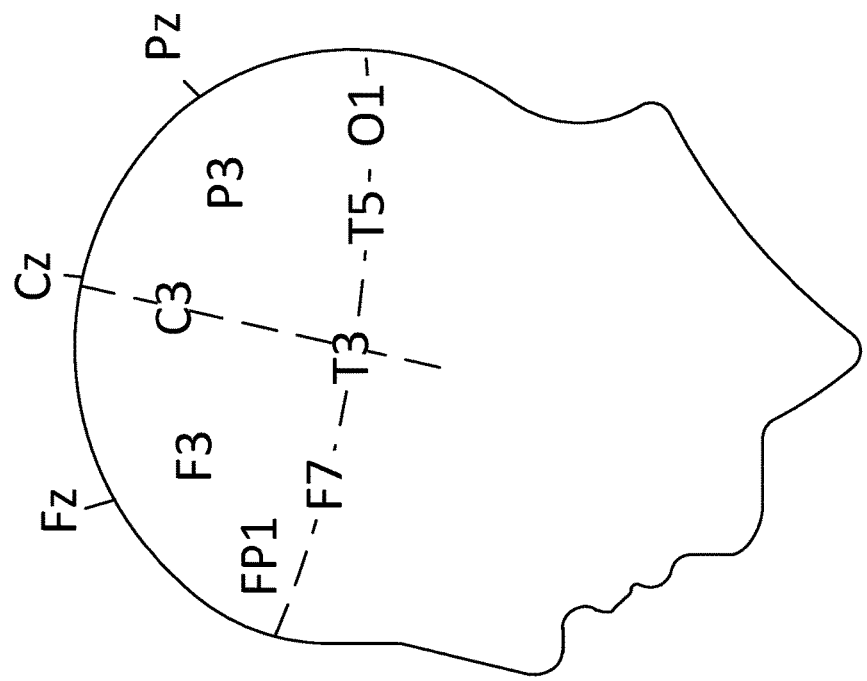

While a patient may be receiving VNS therapy to reduce severity and frequency of seizures, the current methods of quantifying the reduction are generally not very accurate. Now referring to FIGS. 4A and 4B, diagrams showing electrode placement for collecting EEG signals are shown, according to an example embodiment. To determine the severity of a seizure, EEG data can be collected and analyzed to determine a location and amount of electrical activity where a seizure is occurring in the brain. To collect EEG data, an electrode array may be placed on the scalp of a patient. For example, the 10-20 system may be used to determine the placement of the electrodes. Combinations of letters and numbers are used to distinguish the electrodes from one another based on a location of the electrode. In some embodiments, 19-25 electrode channels may be used. However, in other embodiments, more or less electrodes may be used. Parameters that can be measured from the EEG electrodes may include phase, frequency, amplitude, coupling of channels, etc. Alternatively, intracranial electrodes may also be used to obtain EEG data.

Figure 5:
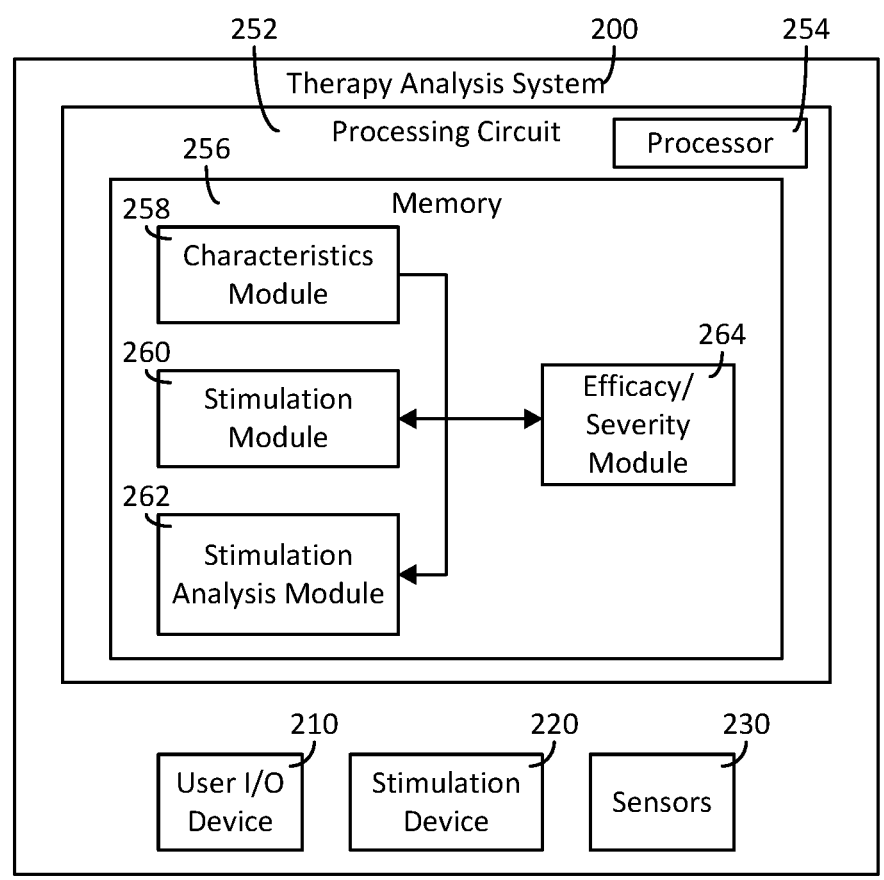
FIG. 5 is a schematic block diagram of a therapy analysis system, according to an example embodiment.

Referring now to FIG. 5, a therapy analysis system 200 may be used to facilitate assessing an efficacy in reducing seizure severity in a patient using vagus nerve stimulation therapy (e.g., determining if a patient is positively responding to VNS). As shown in FIG. 5, the therapy analysis system 200 includes a user input/output (I/O) device 210, a stimulation device 220, one or more sensors 230, and a processing circuit 252. While the device is discussed with respect to analyzing and monitoring VNS therapy, the device may additionally or alternatively be used to assess an efficacy in reducing seizure severity in a patient using other forms of therapy. For example, the analysis system 200 may assess an efficacy in reducing seizure severity in a patient using a drug therapy, or a combination of VNS and drug therapy.

The user I/O device 210 may enable a user of the therapy analysis system 200 to communicate with the therapy analysis system 200 and other components thereof (e.g., the stimulation device 220, etc.). In some embodiments, the user I/O device 210 is communicably coupled to the therapy analysis system 200 via a wireless communication protocol (e.g., Bluetooth, Zigbee, Wi-Fi, radio, cellular, etc.). In some embodiments, the user I/O device 210 is directly communicably coupled to the VNS analysis system 200 (e.g., with a wired connection, etc.). The user I/O device 210 may include an input device and/or a display device. The input device may be configured to allow a user to control the VNS analysis system 200 and/or input various parameters (e.g., stimulation parameters, etc.). The input device may include, but is not limited to, a keyboard, a mouse, a touchscreen device, one or more buttons and switches, voice command receivers, a portable device (e.g., a smart phone, a tablet, a laptop, etc.), etc. The display device may be configured to provide a graphical user interface (GUI) to the user of the therapy analysis system 200. The display device may include, but is not limited to, a touchscreen display, a projector and projection screen, a monitor or television (e.g., a LCD, LED, plasma, DLP, etc.), augmented reality glasses, a portable device (e.g., a smartphone, tablet, laptop, etc.), and/or any other known display devices that can provide a GUI.

The stimulation device 220 may be configured to provide stimulation (e.g., acute, temporary, etc.) during or before a seizure. In one embodiment, the stimulation device 220 includes a lead (e.g., the lead 30, etc.) having at least one electrode (e.g., the electrodes 38, etc.) configured to be positioned proximate to a portion of the vagus nerve 120 (e.g., the cardiac fascicles 126 that branch from the vagus nerve 120, etc.). In another embodiment, the stimulation device 220 includes an external stimulation device configured to be positioned outside the body of the patient to provide the stimulation through the skin of the patient. In one embodiment, the external stimulation device includes an auricular stimulation device configured to provide auricular stimulation around and/or near an ear of the patient. In other embodiments, the external stimulation device includes another type of stimulation device configured to provide stimulation to another external area of the patient (e.g., the chest, the back, the neck, etc.). In still other embodiments, the stimulation device 220 includes a cuff-type electrode (e.g., the cuff-type electrode 40, etc.) or another type of electrode temporarily implanted onto the vagus nerve 120 and configured to provide stimulation directly to the vagus nerve 120 (e.g., VNS, etc.).

The sensors 230 may be configured to acquire response data of a patient having a seizure to facilitate monitoring a physiological response of the patient to VNS therapy during a seizure. The sensors 230 may facilitate monitoring one or more physiological responses of the patient including heart rate change, heart rate variability, EEG, data among other possible responses induced by the seizure. The sensors 230 may also be configured to monitor stimulation levels of the electrode(s) 38 (e.g., current, voltage, power, signal frequency, pulse width, signal ON time, signal OFF time, etc.). The sensors 230 may additionally or alternatively be configured to acquire patient data indicative of one or more physiological characteristics of the patient prior to the seizure. The one or more physiological characteristics acquired by the sensors 230 may include resting heart rate, nocturnal heart rate, heart rate variability (HRV), among other possible measureable physiological characteristics.

As shown in FIG. 5, the processing circuit 252 includes a processor 254 and a memory 256. The processor 254 may be implemented as a general-purpose processor, an application specific integrated circuit (ASIC), one or more field programmable gate arrays (FPGAs), a digital signal processor (DSP), a group of processing components, or other suitable electronic processing components. The memory 256 (e.g., RAM, ROM, Flash Memory, hard disk storage, etc.) may store data and/or computer code for facilitating the various processes described herein. Thus, the memory 256 may be communicably connected to the processor 254 and provide computer code or instructions to the processor 254 for executing the processes described in regard to the VNS analysis system 200 herein. Moreover, the memory 256 may be or include tangible, non-transient volatile memory or non-volatile memory. In some embodiments, the memory 256 may include database components, object code components, script components, or any other type of information structure for supporting the various activities and information structures described herein.

The memory 256 may include various circuits for completing processes described herein. More particularly, the memory 256 includes circuits configured to control operation of the therapy analysis system 200 to assess an efficacy of reducing severity of seizures using VNS therapy. While various circuits with particular functionality may be used, it will be understood that the memory 256 may include any number of circuits for completing the functions described herein. For example, the activities of multiple circuits may be combined as a single circuit and additional circuits with additional functionality may be included. In some embodiments, the circuits of the memory 256 are integrated and/or combined. Further, it will be understood that the processing circuit 252 of the therapy analysis device 200 may further control other processes beyond the scope of the present disclosure.

As shown in FIG. 5, the therapy analysis system 200 includes a characteristics database 258, a stimulation manager 260, a stimulation analyzer 262, and an efficacy/severity analyzer 264. The characteristics database 258 may be configured to receive and store patient data indicative of various physiological characteristics of a patient being assessed for the efficacy of vagus nerve stimulation therapy. The physiological characteristics may include a heart rate, an instantaneous heart rate, EEG and/or ECG data, resting heart rate, among other possible physiological characteristics of the patient. In some embodiments, at least a portion of the physiological characteristics are received by the characteristics database 258 from the sensors 230 (e.g., resting heart rate, nocturnal heart rate, instantaneous heart rate, etc.). In some embodiments, at least a portion of the physiological characteristics are received by the characteristics database 258 from a remote server or device collecting EEG signals (e.g., downloaded therefrom, etc.). As shown in FIG. 5, the characteristics database 258 is communicably coupled to the efficacy/severity analyzer 264. Thus, the characteristics database 258 may provide the physiological characteristics to the efficacy/severity analyzer 264 to perform further analysis.

The efficacy/severity analyzer 264 may be configured to receive and store one or more response features (e.g., change in heart rate percentage, tachycardia duration, etc.) regarding a efficacy of VNS therapy in reducing seizure severity. The one or more response features may be predefined within the efficacy/severity analyzer 264 and/or manually input by an operator of the VNS analysis system 200. The response features may be compared to thresholds, or other response features associated with the patient. The thresholds may be a magnitude difference and/or a percentage difference (e.g., of a post-treatment value relative to a pre-treatment value, etc.). The efficacy/severity analyzer 264 may thereby be configured to receive the information regarding the physiological response of a respective patient to the provided therapy (e.g., from the stimulation analyzer 262, etc.). The efficacy/severity analyzer 264 may further determine the patient's suitability for continuing VNS therapy based on the one or more response features and the one or more physiological responses of the patient being assessed for VNS therapy efficacy. For example, if the change in heart rate of a patient changes more than the change in heart rate change threshold (e.g., in response to the stimulation, etc.), the vagus nerve stimulation therapy may be effective at reducing the severity of seizures for the patient.

In some embodiments, the efficacy/severity analyzer 264 is configured to determine a synchronizability index for electrodes coupled to the VNS analysis system. According to an exemplary embodiment, the efficacy/severity analyzer 264 is configured to determine a VNS therapy is effective in reducing the severity of seizure when less electrodes are determined to contribute to the synchronization due to a seizure. In some embodiments, the efficacy/severity analyzer 264 is configured to compare a number of electrodes that contribute to synchronization due to seizure before VNS therapy to a number of electrodes that contribute to synchronization due to seizure after VNS therapy.

The efficacy/severity analyzer 264 may be further configured to provide an indication of the efficacy of the vagus nerve stimulation therapy via the user I/O device 210. In one embodiment, the indication includes the number of electrodes contributing to synchronization due to seizure. In other embodiments, the indication includes a percentage, a value, and/or another metric indicative of the efficacy of the VNS therapy on the seizures of the patient based on a comparison of pre-treatment severity to post-treatment severity. In other embodiments, the indication includes a diagram indicating locations of the electrodes that contribute to synchronization due to seizure or levels of electrical activity in the brain due to seizure.

Referring back to FIG. 5, the stimulation manager 260 may be configured to control operation of the stimulation device 220 (e.g., the electrodes 38, etc.) to provide stimulation to the vagus nerve of a patient. The stimulation manager 260 may be further configured to monitor and/or control stimulation parameters and/or levels provided by the stimulation device 220 (e.g., current, voltage, power, signal frequency, pulse width, signal ON time, signal OFF time, etc.). In some embodiments, the stimulation manager 260 is configured to control the stimulation device 220 according to a predefined stimulation protocol. In other embodiments, the stimulation manager 260 is configured to control the stimulation device 220 based on manually input control parameters provided by an operator of the therapy analysis system 200.

The stimulation analyzer 262 may be configured to receive response data acquired by the sensors 230 indicative of a physiological response of the patient to the stimulation of the vagus nerve. Therefore, the stimulation analyzer 262 may be configured to monitor one or more physiological responses of the patient to the stimulation including heart rate changes, HRV changes, among other possible responses induced by the stimulation. As shown in FIG. 5, the stimulation analyzer 262 is communicably coupled to the efficacy/severity analyzer 264. Thus, the stimulation analyzer 262 may provide information regarding the physiological response of a patient to the efficacy/severity analyzer 264 to perform further analysis. In another embodiment, the efficacy/severity analyzer 264 may provide information to the stimulation manager 260 or the stimulation analyzer 262 in order to modify parameters of the stimulation based on the efficacy of VNS therapy in reducing seizure severity.

Figure 6A:
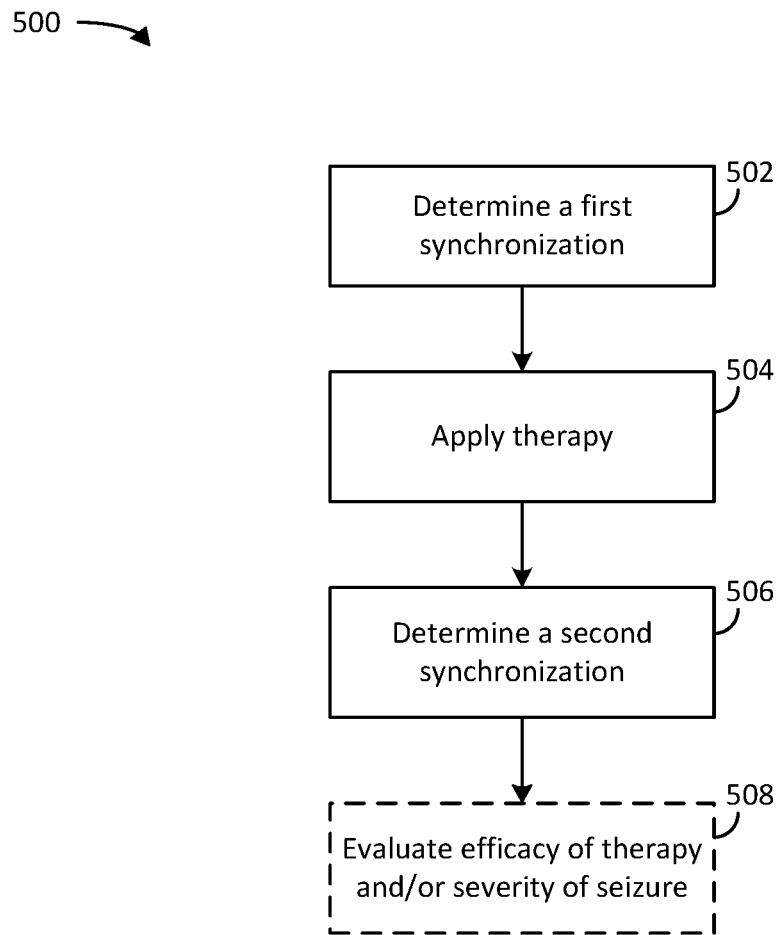
FIGS. 6A-6B are flow charts of methods of measuring a severity of a seizure and an efficacy of VNS therapy, according to an example embodiment.
Figure 6B:
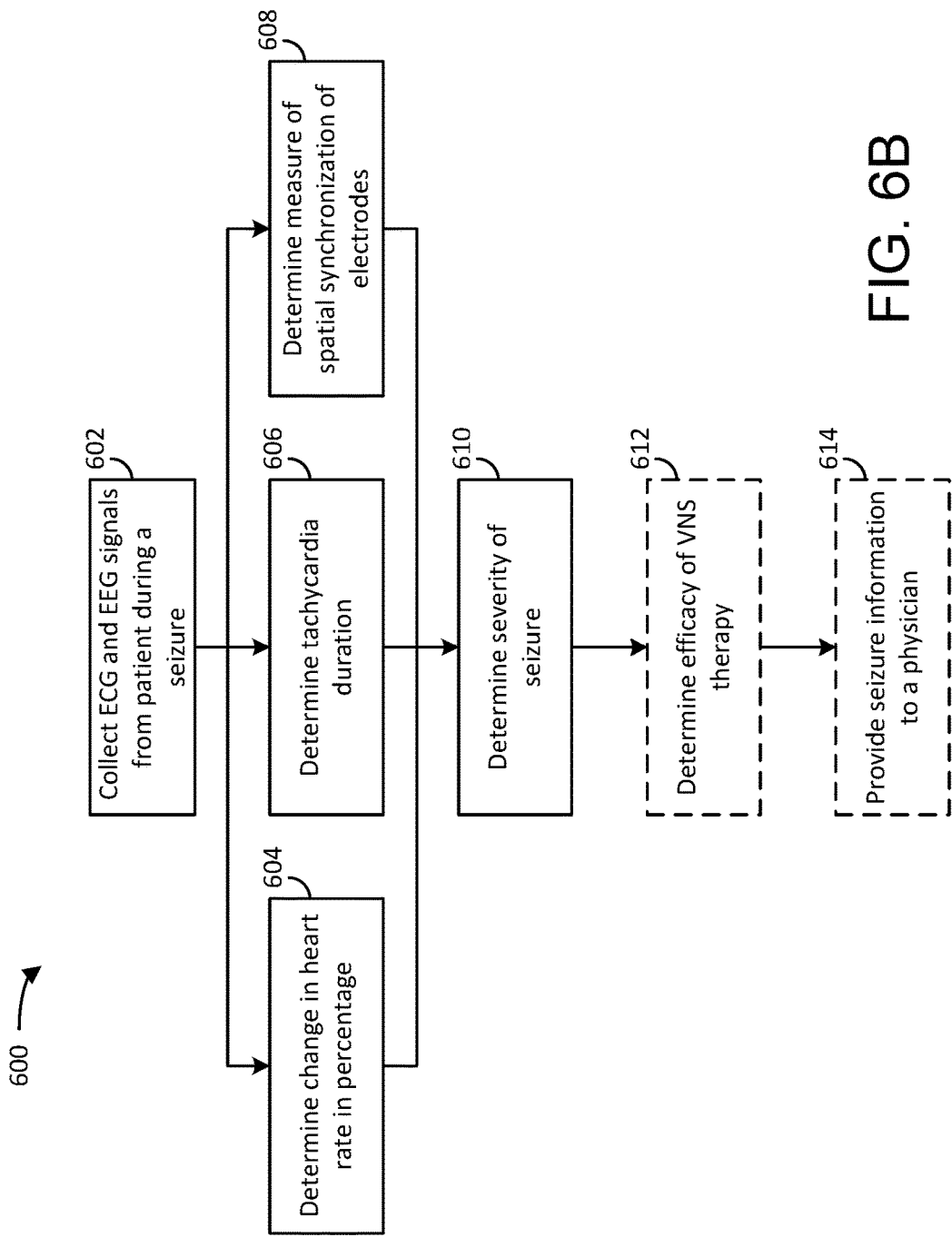

FIGS. 6A-6B are flow charts of methods 500 and 600, respectively, of measuring a severity of a seizure and an efficacy of VNS therapy, according to an example embodiment. Method 500 includes determining a first synchronization, applying a therapy, determining a second synchronization and in some embodiments, evaluating an efficacy of treatment or a severity of seizure. Method 600 includes collecting EEG and ECG data during a seizure, measuring parameters of the data, and using the measurements to determine an efficacy of the VNS therapy and a severity of the seizure. Methods 500 and 600 may also include providing location information of synchronized electrodes to a physician.

Methods 500 and 600 may be performed one or more times. For example, method 500 may be performed with different therapies applied, such as VNS therapy with different stimulation parameters or a drug therapy with different doses. Method 600 may be performed prior to a patient receiving VNS therapy and after the patient has received VNS therapy. In some embodiments, method 600 may be performed multiple times prior to a patient receiving VNS therapy and after the patient has received VNS therapy. In another embodiment, method 600 may be performed multiple times after the patient has received VNS therapy. The methods 500 and 600 may be performed at a given interval (e.g., once a month, every two months, etc.).

Referring to method 500, a first synchronization of a first seizure is determined at 502. The first synchronization may be determined by collecting EEG signals from EEG electrodes (e.g., placed on the scalp of a patient as described with respect to FIGS. 4A and 4B) and analyzing the EEG signals across all electrodes to determine a spatial synchronization (e.g., per the method described in FIGS. 9 and 10). In some embodiments, the first synchronization is determined prior to applying any therapy. In another embodiment, the first synchronization is determined after receiving a first therapy.

A therapy is applied at 504. The therapy may be a VNS therapy, a drug therapy, or a combination thereof. While these are common therapies for epilepsy, other therapies or treatments may be applied as well, such as surgery, a ketogenic diet, or other forms of stimulation. The therapy applied may be a first therapy with a first set of parameters (e.g., stimulation parameters, dosage parameters, etc.). In another embodiment, the therapy applied may be a therapy other than the first therapy. If the therapy applied is not the first therapy, a second set of parameters may be used that are different from the first set of parameters. In some embodiments, the first and second therapies may not be the same type of therapy.

A second synchronization of a second seizure is determined at 506. The second synchronization may be determined using the same techniques as determining the first synchronization at 502.

In some embodiments, a efficacy of therapy and/or a severity of seizure may be evaluated at 508. The efficacy of therapy and/or severity of seizure may be evaluated by comparing the first synchronization to the second synchronization. In some embodiments, the efficacy of therapy and/or severity of seizure may be determined by comparing the first synchronization, the second synchronization, or both the first and second synchronization to a threshold. The severity of seizure may be evaluated separately based on the first and second synchronization, or as a change in severity based on both the first and second synchronization. Additional methods for evaluating the efficacy of therapy and/or a severity of seizure are described with respect to FIG. 6B.

Now referring to method 600, as discussed above, the vagus nerve stimulator 10 may be equipped with a heart rate sensor to collect ECG signals at 602. In some embodiments, electrodes may be placed on the patient's limbs or chest to collect ECG signals. Epileptic seizures can lead to changes in autonomic function affecting the sympathetic, parasympathetic, and enteric nervous systems. Changes in cardiac signals are potential biomarkers that may provide an extracerebral indicator of ictal onset in some patients.

Heart rate can be measured easily when compared to other cardiac biomarkers (e.g., ST segment elevation, T-wave alternans), and therefore may be used to assess the effect of seizures on cardiovascular function. Understanding the magnitude and duration of heart rate changes associated with seizures may be used to determine the effect of a therapy on cardiovascular dynamics during seizures. However, ECG signals are typically affected by muscle/motion artifacts and therefore, it becomes difficult to estimate actual changes in heart rate in an automated manner. Analysis of the ECG data will be discussed more with respect to FIG. 7.

EEG data is collected using the EEG electrodes or sensors placed on the scalp of a patient (e.g., as described with respect to FIGS. 4A and 4B) at 602. When measuring on the scalp of the patient, electrical activity of neurons in the brain is diffused through layers of tissue and the skull before reaching an electrode. This causes electrical activity to show up on multiple channels or electrodes, allowing the electrical fields to be mapped. However, this also causes dilution of the specific location of the neural activity, such as the neural activity seen during a seizure. To compensate for this phenomena, the electrode channels are decorrelated to determine independent sources of activity. This will be described below with respect to FIGS. 8-11.

The ECG data and EEG data are used to determine change in heart rate in percentage at 604, tachycardia duration at 606, and determine a measure of spatial synchronization of electrodes at 608. Each of these methods will be described in detail herein according to exemplary embodiments.

The measurements can be used to determine a severity of the seizure at 610 and/or an efficacy of the VNS therapy at 612. If a single set of measurements are determined (i.e., method 600 occurred once), the severity of the seizure may be determined using the measurements. This will be described in further detail herein. If method 600 is performed multiple times, the severity of each seizure and the efficacy of the VNS therapy may be determined. The efficacy and/or severity of the VNS therapy may be determined by comparing two or more sets of measurements. In another embodiment, the efficacy and/or severity may be determined by comparing the sets of measurements to a plurality of thresholds. For example, a single threshold may be used, wherein a comparison of the measurements to the threshold indicates "severe" or "not severe" for severity of seizure, and "effective" or "not effective" for efficacy of therapy. In another embodiment, multiple thresholds may be implemented. For example, when determining severity, a comparison to a first threshold and second threshold may indicate "severe," "moderately severe" and "not severe." For example, when determining efficacy, when the difference between the measured synchronization before and after treatment is above a first value, "very efficacious" or an indicator indicating a higher level of efficacy may be indicated, when the difference is above a second value, "somewhat efficacious" or an indicator indicating a moderate level of efficacy may be indicated and when the difference is below the second value, "not efficacious" or an indicator indicating a low level of efficacy may be indicated. However, more or less thresholds may be used to indicate varying levels of severity and/or efficacy. The thresholds may be user specific, or may be based on data from a population of patients. The efficacy of VNS therapy may be determined by performing statistical tests (e.g., t-test, f-test, etc.) on the measured parameters. The efficacy and/or severity may be determined by a physician observing the measured parameters. In some embodiments, the efficacy and/or severity is determined by a combination of the aforementioned methods.

Method 600 may also include providing seizure information to a physician. The information provided to the physician may include the severity of the seizures, the efficacy of the VNS therapy, the location of the synchronized channels, etc. The information provided to the physician will be described in more detail with respect to FIGS. 9-12.

Figure 7:
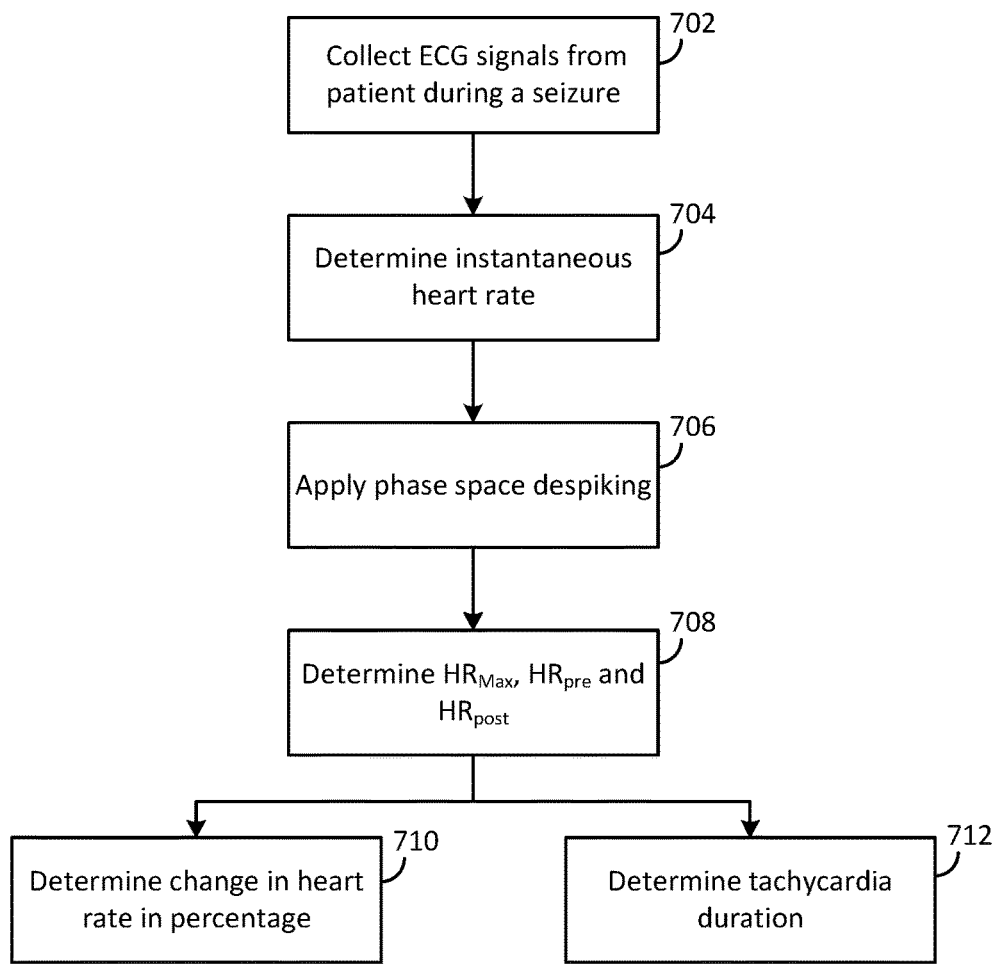
FIG. 7 is a flow chart of a method of analyzing ECG data according to FIG. 6, according to an example embodiment.

Now referring to FIG. 7, a flow chart of a method 700 of analyzing ECG data according to FIG. 6 is shown, according to an example embodiment. The ECG data is analyzed to determine the heart rate change, in percentage, during a seizure, and the duration of increased heart rate during a seizure.

A raw ECG signal is collected using the ECG electrodes or the heart rate sensor as discussed above at 702. The raw ECG signal can be seen in FIG. 8A.

A despiking algorithm is applied to the ECG signal in order to remove artifacts from the heart rate (HR) signal. This may be achieved by first extracting an RR-interval, a time interval between the peaks of two adjacent R waves from the ECG signal, and calculating an instaneous heart rate (IHR) (i.e., IHR=60/(RR-interval)) at 704.

Figure 8A:
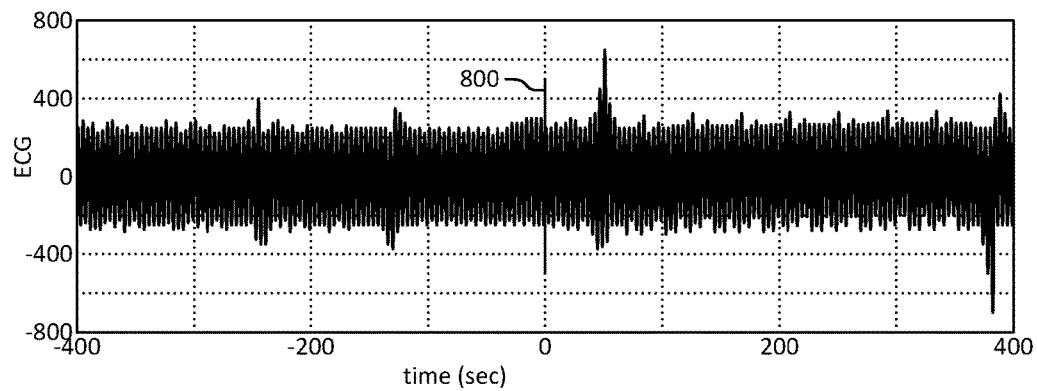
FIG. 8A is an ECG signal versus time, according to an example embodiment.
Figure 8B:
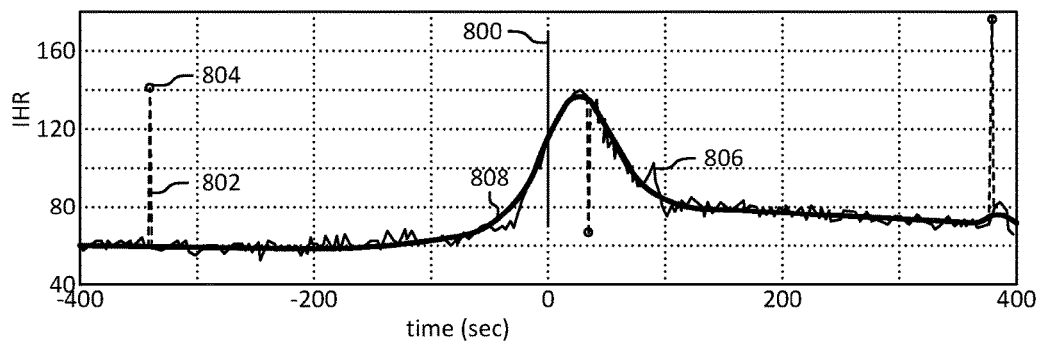
FIG. 8B is an instantaneous heart rate (IHR) verses time corresponding to the ECG signal of FIG. 8A, before and after despiking, according to an example embodiment.
Figure 8C:
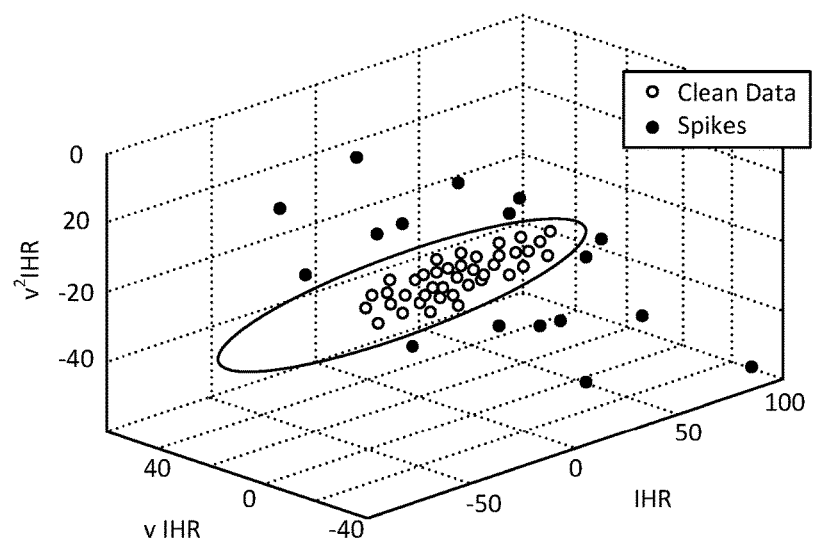
FIG. 8C is a phase-space plot showing a phase space despiking approach of the ECG signal of FIG. 8A, according to an example embodiment.

A phase space despiking is applied to the instantaneous heart rate at 706. FIG. 8B shows the instantaneous heart rate (IHR) verses time corresponding to the ECG signal of FIG. 8A, before and after despiking. The phase space despiking approach includes constructing an ellipsoid in three-dimensional phase space, and identifying spikes as points that are outside of the ellipsoid. The method iterates until a number of new points identified as spikes fall to zero. This approach is illustrated in FIG. 8C and the steps per iteration are outlined below:

1) From the original time series $u_i$ (e.g., HR) a first and second derivative is approximated as $$\nabla u_i = (u_{i+1} - u_{i-1})/2 \qquad (1)$$

$$\nabla^2 u_i = \frac{\nabla u_{i+1} - \nabla u_{i-1}}{2} \qquad (2)$$

2) The standard deviations of all three variables, $\sigma_u$, $\sigma_{\nabla u}$, and $\sigma_{\nabla^2 u}$ is calculated, and the expected maxima is calculated using the Universal criterion, $\mu_u \hat{\sigma} = \sqrt{2\ln n}\hat{\sigma}$, where n is the number of time samples in u, $\mu_u \sqrt{2\ln n}$ is the Universal threshold, and $\hat{\sigma}$ is the estimated standard deviation.

3) The rotation angle of the principal axis of $\nabla^2 u_i$ versus $u_i$ is calculated using the cross correlation:

$$\theta = \tan^{-1}(\Sigma u_i \nabla^2 u_i / \Sigma u_i^2) \quad (3)$$

(Note: for $\nabla u_i$ versus $u_i$ and for $\nabla^2 u_i$ versus $\nabla u_i, \theta \approx 0$ because of symmetry.)

4) For each pair of variables, the ellipse that has maxima and minima from $u_i$, $\nabla u_i$, and $\nabla^2 u_i$ is calculated. Thus, for $\nabla u_i$ versus $u_i$, the major axis is $\mu_u \sigma_u$ and the minor axis is $\mu_u \sigma_{\nabla u}$; for $\nabla^2 u_i$ versus $\nabla u_i$ the major axis is $\mu_u \sigma_{\nabla u}$ and the minor axis is $\mu_u \sigma_{\nabla^2 u}$; and for $\nabla^2 u_i$ versus $u_i$; the major and minor axes, a and b, respectively, can be shown to be the solution of $$(\mu_u \sigma_u)^2 = a^2 \cos^2 \theta + b^2 \sin^2 \theta \quad (4)$$

$$(\mu_u \sigma_{\nabla^2 u})^2 = a^2 \sin^2 \theta + b^2 \cos^2 \theta \quad (5)$$

5) For each projection in phase space, the points that lie outside of the ellipse are identified and replaced using the cubic polynomial interpolation.

At each iteration, replacement of the spikes reduces the standard deviations calculated in step 2 and thus the size of the ellipsoid reduces until further spike replacement has no effect. FIG. 8A shows an example of the recorded ECG from a left temporal lobe seizure. Vertical line 800 (at time 0sec) indicates a start time of the seizure. Trace 802 in FIG. 8B shows the corresponding instantaneous heart rate (IHR). FIG. 8B shows the spikes in the IHR (marked with circles (e.g., circle 804)) that could be due to the erroneous detection of noise/artifacts in the ECG signal. Following the application of the despiking algorithm, a trace 806 in FIG. 8B shows the despiked IHR. The despiked HR is then smoothed using the pseudo-Gaussian smoothing (e.g., with a window of size 5), as seen as trace 808 in FIG. 8B, prior to estimation of HR change percentage and duration associated with the seizure.

Figure 8D:
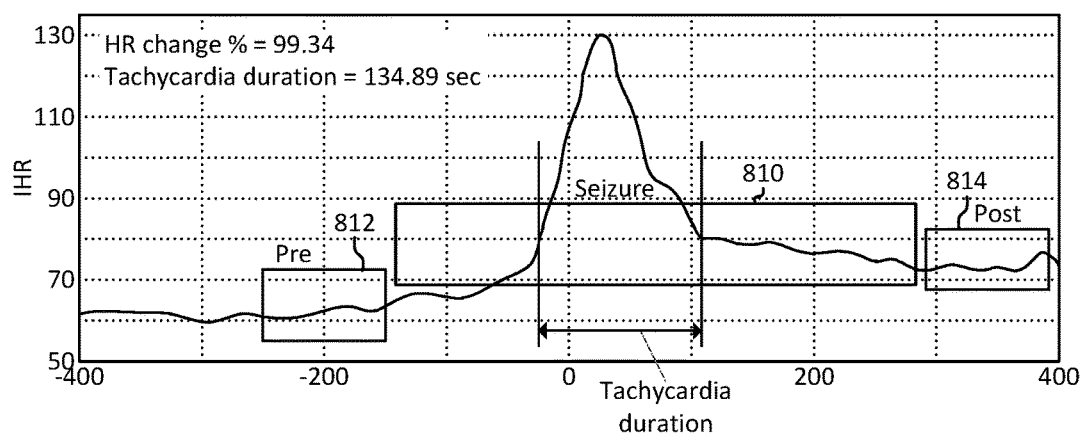
FIG. 8D is a smoothed version of the IHR of FIG. 8B, according to an example embodiment.

Using the smooth despiked HR, $HR_{Max}$, $HR_{pre}$ and $HR_{post}$ are determined at 708. The maximum of IHR change ($HR_{Max}$) is found using the despiked IHR in a time window (defined as seizure window 810 hereafter) (e.g., 450 sec), extending from a time period (e.g., 150 sec) before a seizure annotation (time 0 in FIG. 8D) to a time period (e.g., 300 sec) after the annotation. In addition, the mean of IHR in a pre-ictal window 812 and a post-ictal 814 window is calculated, namely $HR_{pre}$ and $HR_{post}$ respectively. The pre-ictal window 812 may immediately precede the seizure window 810 and may last a predetermined amount of time (e.g., 100 sec). In addition, the post-ictal window 814 may immediately follow the seizure window 810 and may last a predetermined amount of time (e.g., 100 sec). While the pre-ictal window 812 and the post-ictal window 814 are shown to immediately precede and follow the seizure window 810, there may be a time delay between the pre-ictal and post-ictal windows and the seizure window. In some embodiments, the pre-ictal and post-ictal windows are the same amount of time, as shown in FIG. 8D. In another embodiment, the pre-ictal and post-ictal windows span different amounts of time. The HR change percentage is calculated as HR change % = $(HR_{max} - HR_{pre})/HR_{pre} \times 100$ at 710. In addition, a tachycardia duration (TCD) is calculated at 712. TCD is estimated as a difference between the time of a first IHR value that is lower than $HR_{pre}$ in the values preceding $HR_{Max}$ and a first IHR value that is lower than $HR_{post}$ in the values following $HR_{Max}$. The HR change % and TCD are estimated per seizure and used as two cardiac-based features for quantifying a severity of one or more seizures. While the change in heart rate percentage and the tachycardia duration are used as the two cardiac-based features for quantifying seizure severity, other cardiac parameters could be used in addition, or in place of these features. In some embodiments, only one cardiac-based feature is used to quantify seizure severity. In other embodiments, more than two cardiac-based features may be used to quantify seizure severity. Further, it should be appreciated that the process described above with respect to FIG. 7 is only one example method for processing the ECG data; other methods of processing the ECG data may be utilized in other embodiments and fall within the scope of the present disclosure.

In addition to affecting heart rate, epileptic seizures are manifestations of intermittent spatiotemporal transitions of the human brain from the interitcal state to the ictal state. Dynamical analysis of EEGs at multiple sites of the epileptic brain has shown a progressive change in synchronization prior to and during epileptic seizures. Thus, one could postulate that if a therapy is effective, it would alter the synchronization of brain dynamics. One issue that affects the measurement of synchronization using scalp EEGs is that most closely-spaced EEG electrodes appear to be always correlated due to the common-source of activity that they receive from deep brain sources that are immediately underneath or spatially distant. These spatially distant sources tend to artificially increase the value of synchronization. Methods of independent component analysis and principal component analysis may be used to address this issue; however, these methods transform the electrode-space into a new set of basis functions that may not have any clinical relevance. Due to this reason, it becomes difficult to clinically interpret the synchronization values provided by applying bivariate (pair-wise) approaches of measuring brain synchrony such as cross-correlation, phase synchronization on the transformed signal space. To resolve this issue, synchronization in the electrode space can be estimated by measuring the contribution of each electrode to the global network synchronization, a quantity defined as a synchronizability of the electrode.

Figure 9:
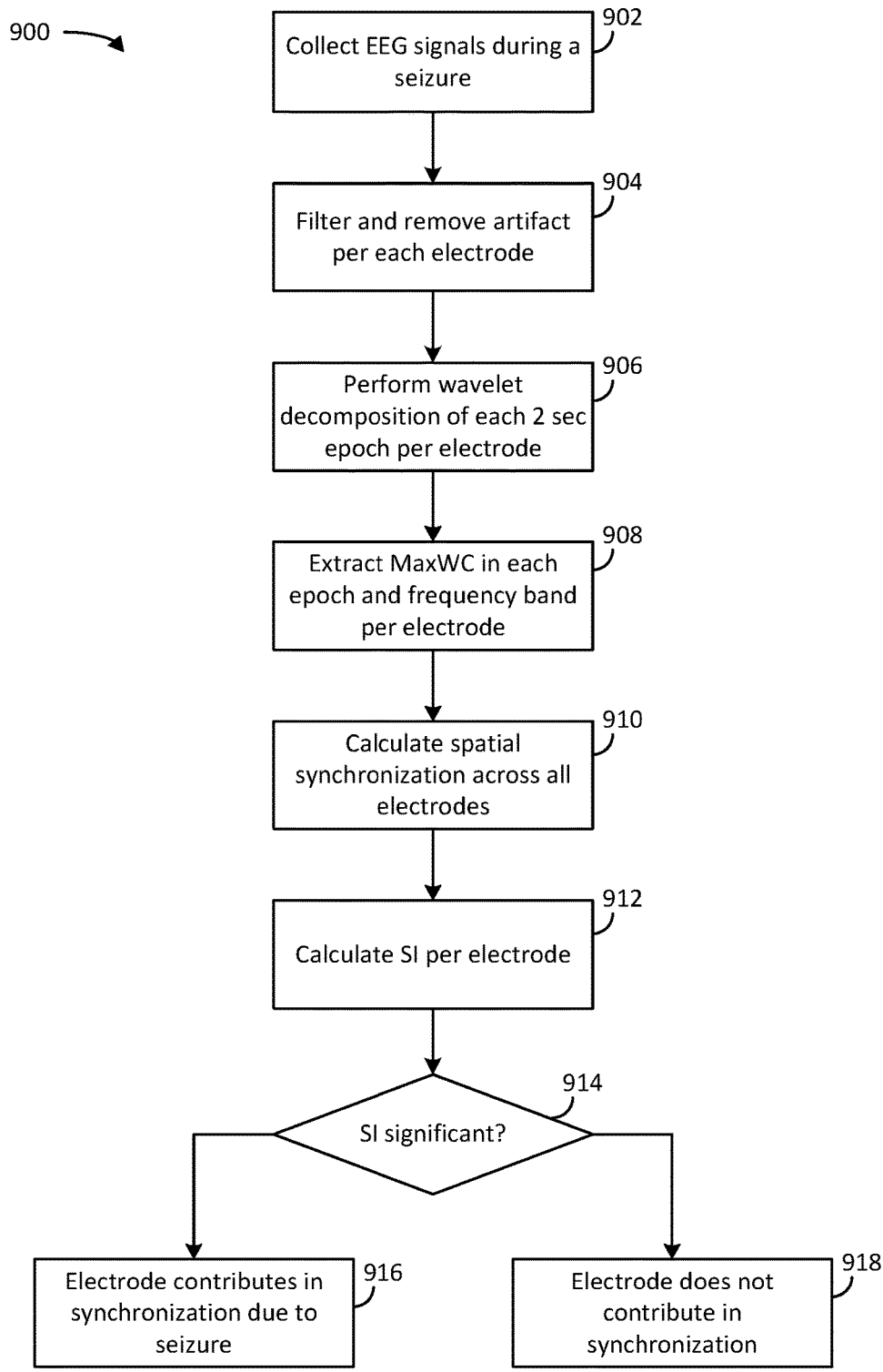
FIG. 9 is a flow chart of a method of determining a synchronizability of each EEG electrode and a number of synchronized EEG electrodes according to FIG. 6, according to an example embodiment.
Figure 10:
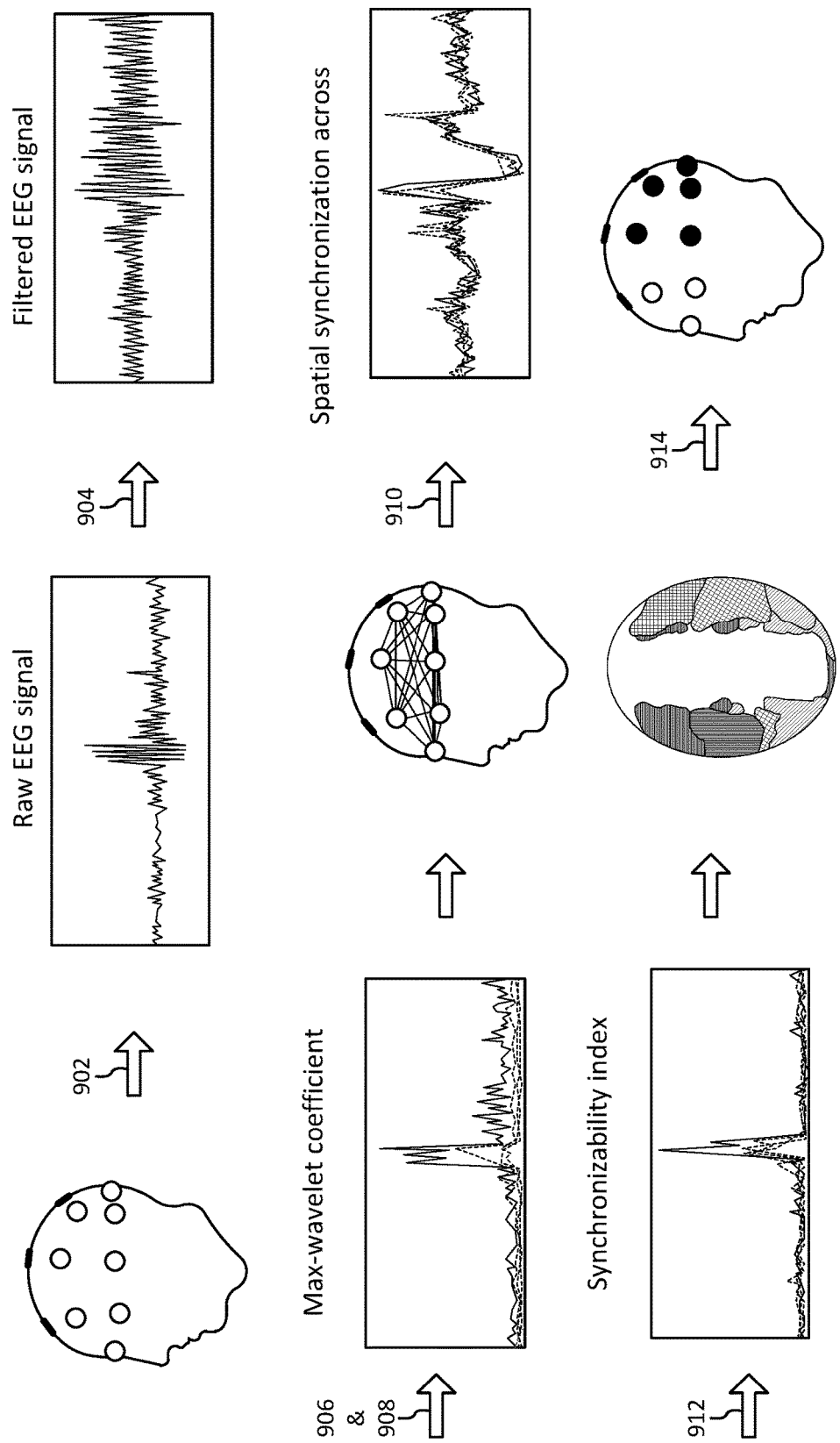
FIG. 10 is the method of FIG. 9, shown in images, according to an example embodiment.

FIG. 9 is a flow chart of a method 900 of determining a synchronizability of each EEG electrode and a total number of synchronized EEG electrodes, according to an exemplary embodiment. Method 900 includes a plurality of equations for determining a synchronizabiltiy of each electrode. However, these calculations and equations are not meant to be limiting and are provided only by way of example. Other equations or calculations that identify or estimate a contribution of individual electrodes to a synchronization may be used without departing from the scope of the present disclosure. FIG. 10 is a visual illustration of various operations of the method 900 shown in images to illustrate how a physician may see or interpret the data, according to an example embodiment.

EEG signals are collected for a patient during a seizure at 902. The electrodes may be arranged on a head of the patient similar to the configuration shown in FIGS. 4A and 4B. However, other configurations may be used and are intended to fall within the scope of this disclosure. The EEG signal may be segmented into non-overlapping time periods or epochs (e.g., 2 seconds).

For each electrode, the EEG signal is filtered and artifacts are removed at 904. A bandpass filter may be used (e.g., between 0.5 and 30 Hz). In some embodiments, a high pass filter is used. In another embodiment, a low pass filter is used. In yet another embodiment, a combination of filters may be used to filter the EEG signal. EEG high amplitude artifacts may be removed using an artifact-blocking (AB) algorithm. This is a technique that enables artifact removal without eliminating any epoch of the signal. Since the EEG is non-stationary in general, it may be appropriate to use the time-frequency domain methods like an discrete wavelet transform (DWT) analysis to describe EEG in the time and frequency domain (e.g., Daubechies-4 wavelet for the analysis of epileptic EEG). However, other methods of artifact removal may be used.

Wavelet decomposition of each epoch is performed for each electrode at 906. In some embodiments, to decompose the wavelets, the EEG data is decomposed into four frequency sub-bands of δ(e.g., 0 Hz-4 Hz), θ(e.g., 4 Hz-7 Hz), α (e.g., 8 HZ-15 HZ), and β(e.g., 16 Hz-30 Hz). However, few or less frequency sub-bands may be used in other embodiments. For example, a γ(>30 Hz) frequency may be included. In some embodiments, frequency sub-bands may be combined into larger frequency sub-bands (e.g., 0 Hz-7 Hz and 8 Hz to 30 Hz). In another embodiment, the sub-bands may be broken down into narrower frequency ranges. In some embodiments, the sub-bands may have different ranges (e.g., α is 7 Hz-14 Hz).

Figure 11A:
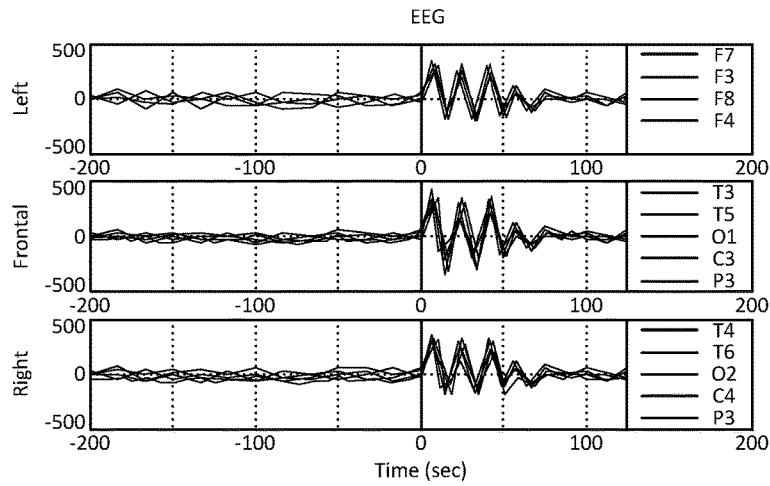
FIG. 11A is a raw EEG recording, according to an example embodiment.
Figure 11B:
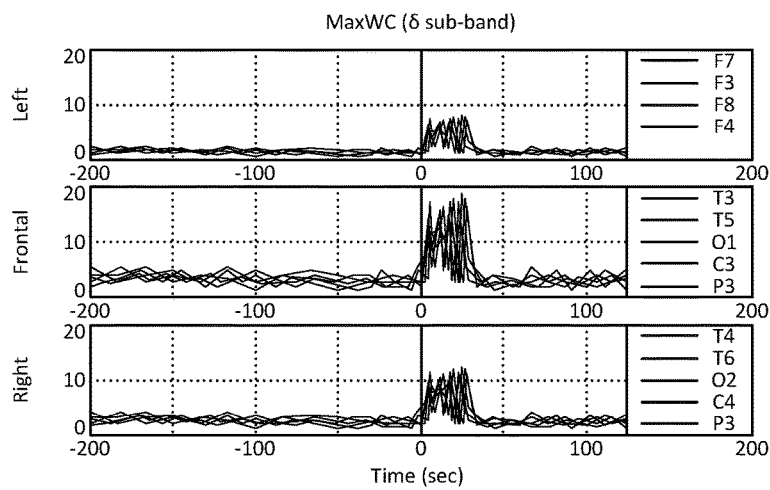
FIG. 11B is a graph of the maximum wavelet coefficients (MaxWC) in the δ frequency sub-band, according to an example embodiment.

Maximum wavelet coefficients (MaxMC) are extracted at 908. The MaxWC in each sub-band for each epoch is used as a feature to represent the time-frequency distribution of EEG signals for that epoch. This results in a time profile of MaxWC values per EEG electrode. FIG. 11A shows the raw EEG signal across multiple electrodes centered around a seizure and the corresponding MaxWC in δ frequency sub-band is shown in FIG. 11B. From these figures, it can be seen that MaxWC attains higher values during a seizure than baseline activity. Furthermore, the values of MaxWC of FIG. 11B are higher in the left hemisphere which is consistent with the seizure focus (left temporal lobe) in this example embodiment. While the MaxWC is used, other features of the decomposed wavelets may be used (e.g., average).

A spatial synchronization across all electrodes is calculated at 910. The synchronizability of each EEG electrode is defined as the contribution that each electrode makes to the global network synchronization. The global spatial synchronization across all electrodes per frequency sub-band is calculated by estimating the ratio of maximum to minimum singular value of the wavelet coefficients x electrodes matrix. Thus, for each sub-band d and epoch k, the global spatial synchronization $\tilde{\theta}_k^d$ may be defined as $$\tilde{\theta}_k^d = \sigma_r^d(k)/\max_k(\sigma_r^d(k)) \quad (6)$$

$$\sigma_r^d(k) = \frac{\max(\sigma^d(k))}{\min(\sigma^d(k))} \quad (7)$$

where $\sigma^d(k)$ is the singular values vector of wavelet coefficients of the $k^{th}$ epoch in sub-band d and $\sigma_r^d(k)$ is the ratio of the maximum to the minimum of the singular values. Since $\tilde{\theta}_k^d$ is a normalized form of $\sigma_r^d(k)$, therefore $\tilde{\theta}_k^d \in [0,1]$. When a seizure occurs, the synchronization among electrodes increases and results in a higher value of $\tilde{\theta}_k^d$. The global synchronization $\tilde{\theta}_k^d$ is used to weigh the wavelet power contribution of each electrode. In order to accomplish this, a relative index of MaxWC per electrode may be created. Thus, in some embodiments, for each value of $\text{MaxWC}^d(k, j)$ for epoch k, electrode j and sub-band d (d=δ, θ, α, or β) the relative index is defined as $$\tilde{g}_{k,j}^d = \frac{\text{Max}WC^d(k, j)}{\text{Max}WC_{ref}^d(j)} \quad (8)$$

where $\text{MaxWC}_{ref}^d(j)$ is the moving average of MaxWC points in the window [k-5,k-20] of electrode j. Since, similar values of $\tilde{g}_{k,j}^d$ across different patients or even different electrodes of the same patient may represent different brain states (i.e. seizure vs. non-seizure), the value of $\tilde{g}_{k,j}^d$ may be scaled using the following nonlinear scaling function g: $R^2 \rightarrow [0,1]$ $$g_{k,j}^d = \begin{cases} 0, & \text{if } \tilde{g}_{k,j}^d < 0.05 \\ \frac{\tilde{g}_{k,j}^d}{10}, & \text{if } 0.05 < \tilde{g}_{k,j}^d < 10 \\ 1, & \text{if } \tilde{g}_{k,j}^d > 10 \end{cases} \quad (9)$$

Figure 11C:
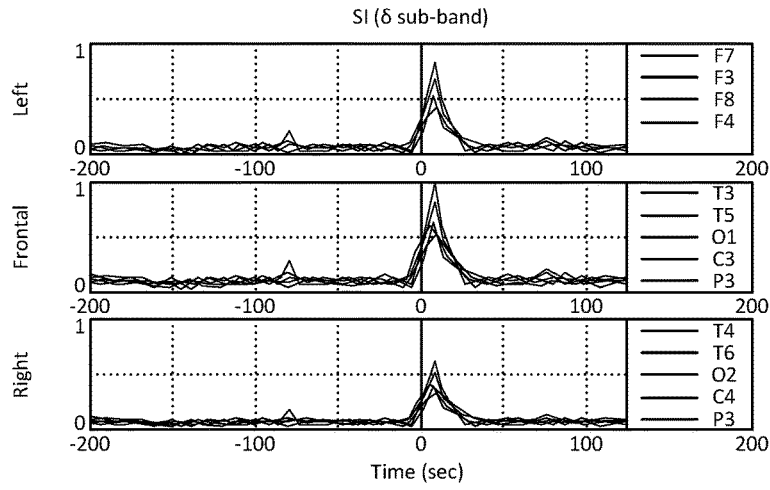
FIG. 11C is an synchronizability index in the δ frequency sub-band, according to an example embodiment.
Figure 12A:
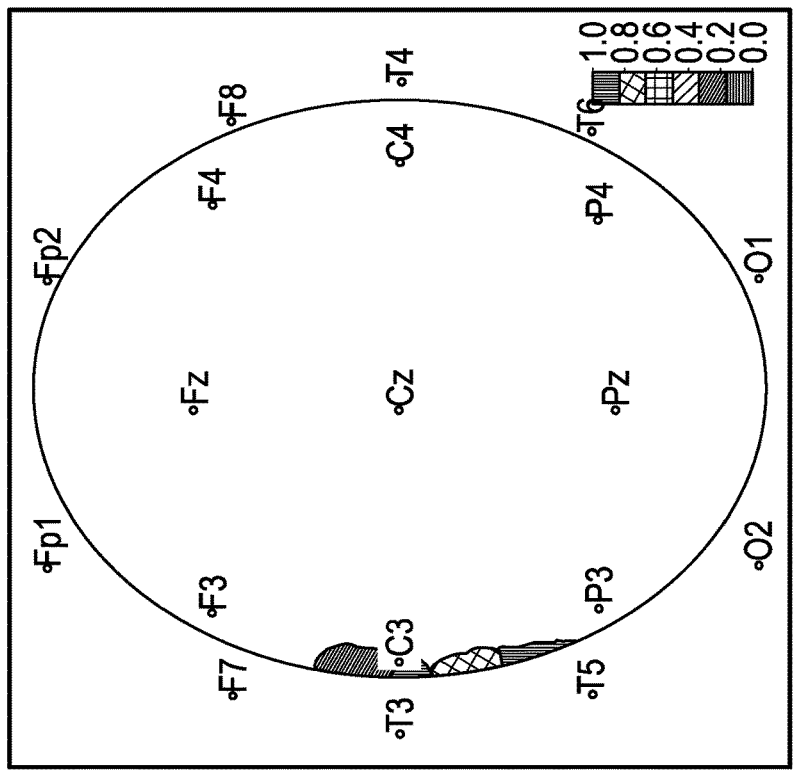
FIGS. 12A, 12C, 12E and 12G are images of a wavelet coefficient change as a result of seizure before VNS therapy, according to an example embodiment.
Figure 12B:
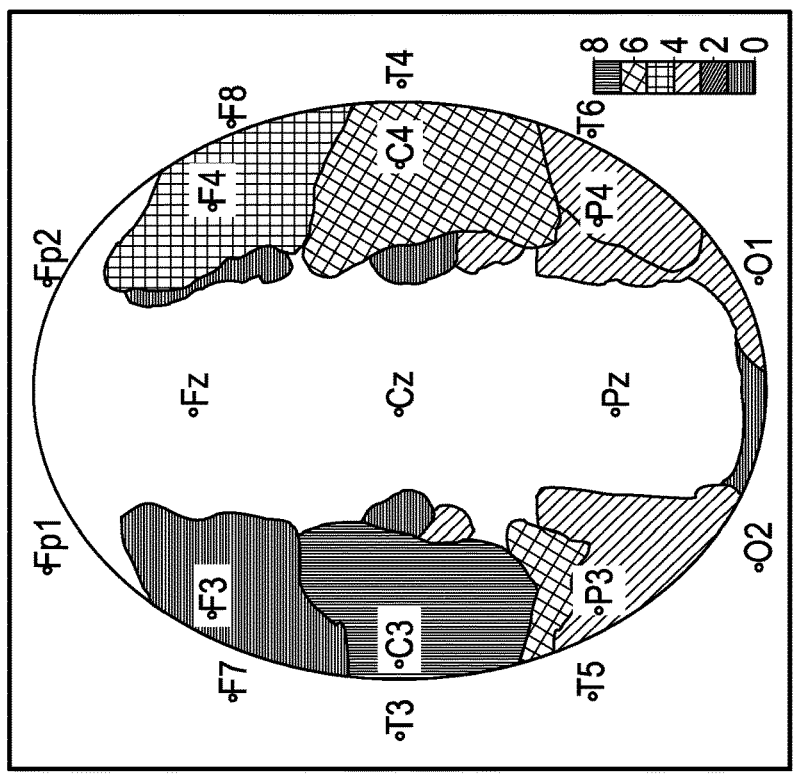
FIGS. 12B, 12D, 12F and 12H are images of a wavelet coefficient change as a result of seizure after VNS therapy, according to an example embodiment.
Figure 12D:
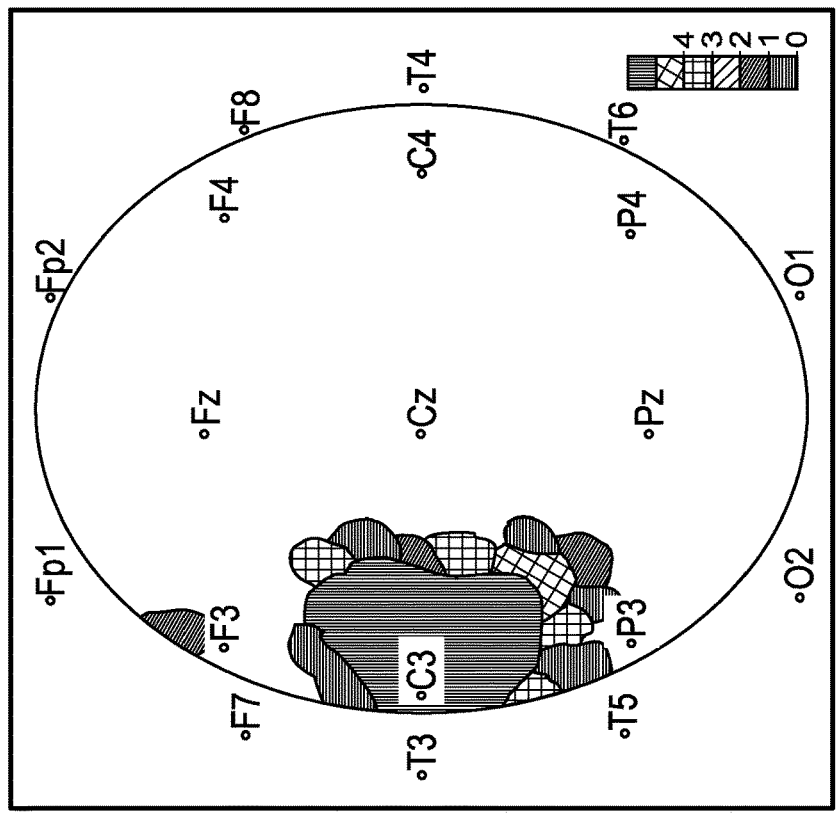
Figure 12C:
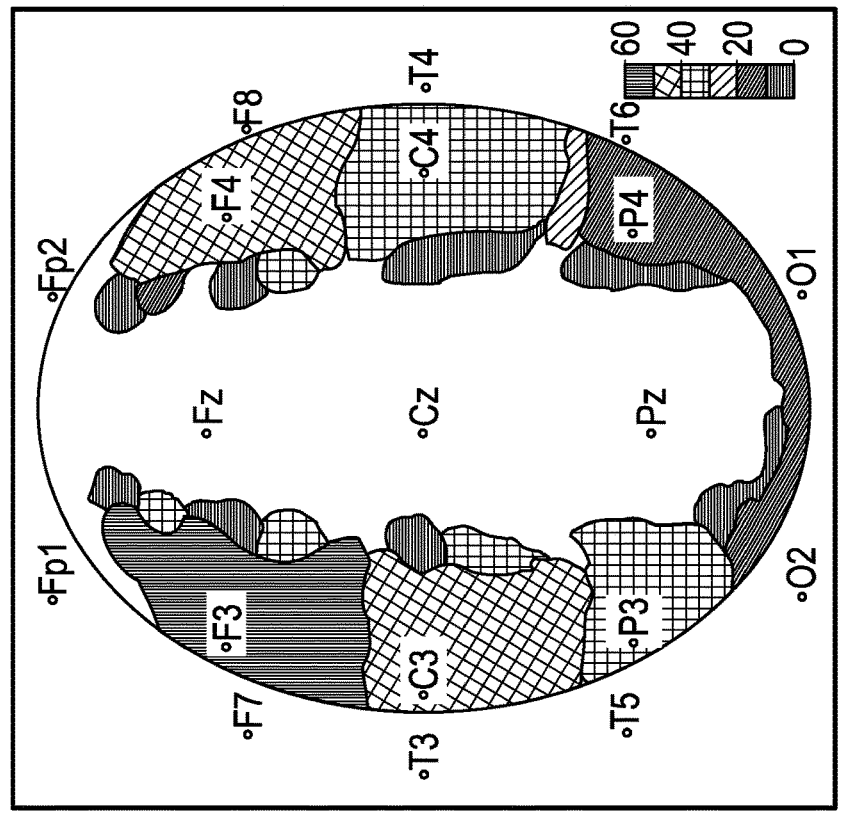
Figure 12F:
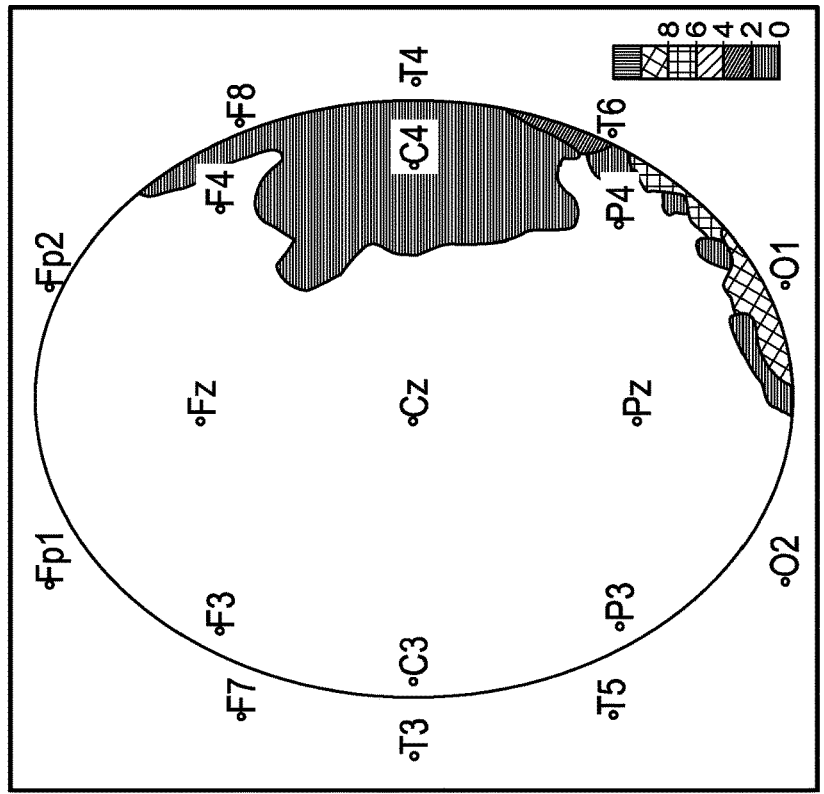
Figure 12E:
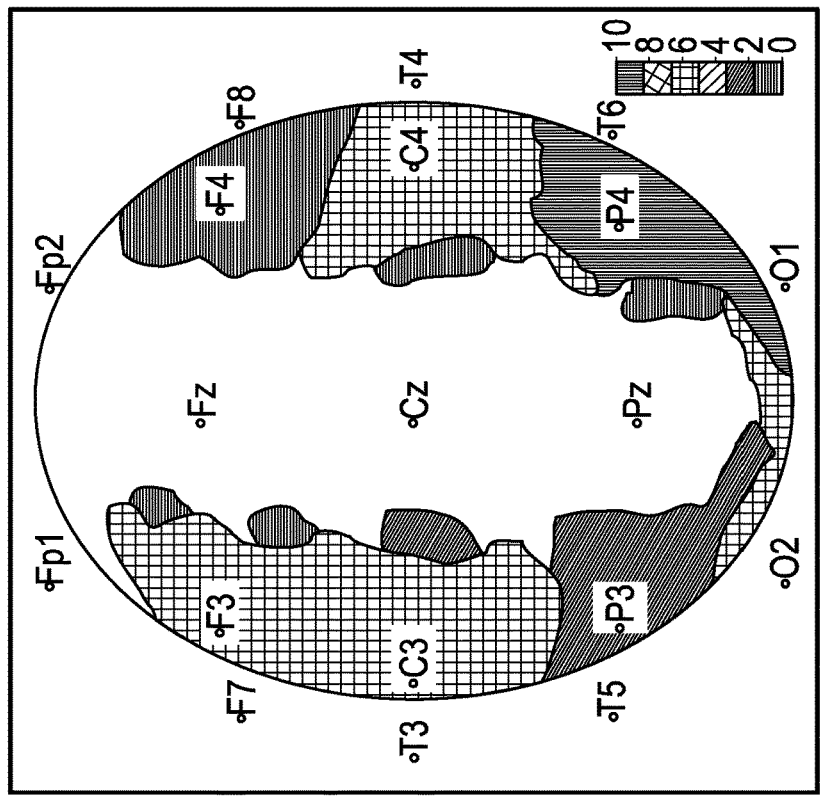
Figure 12H:
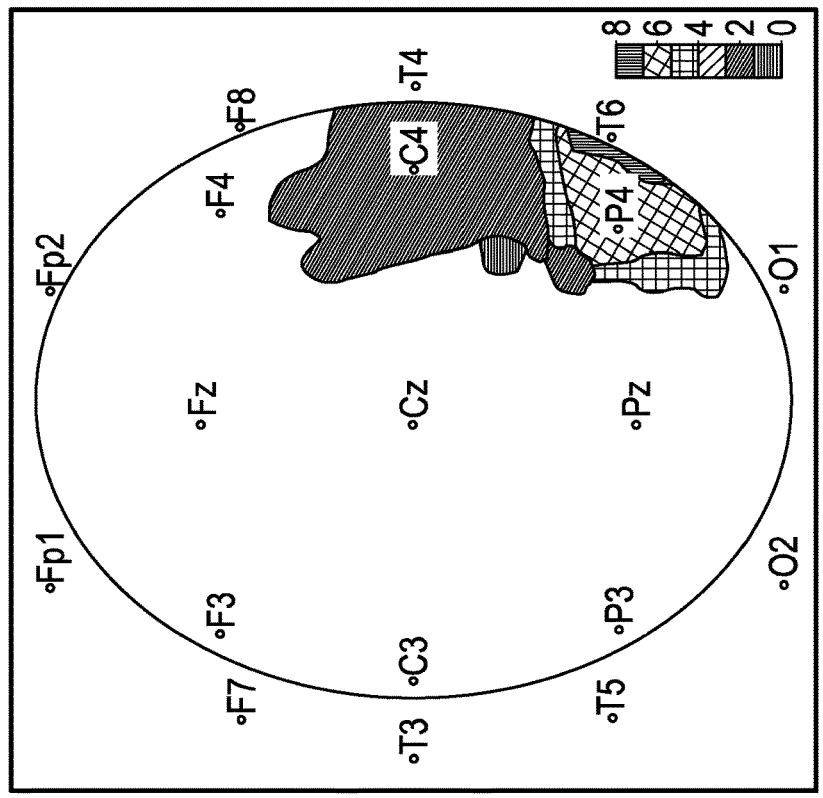
Figure 12G:
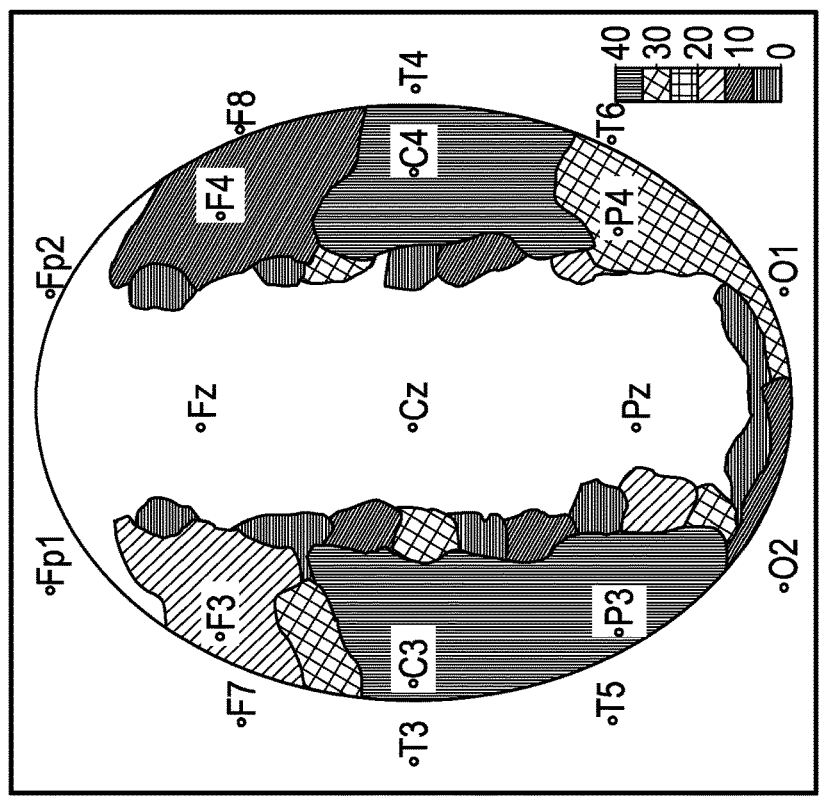

Using the spatial synchronization across all electrodes per frequency, a synchronizability index (SI) is estimated at 912. According to some embodiments, the synchronizability index is estimated per electrode j and epoch k for sub-band d as $$SI_{k,j}^d = (g_{k,j}^d)^{\theta_k^d} \quad (10)$$

where $\theta_k^d = \Omega - (\tilde{\theta}_k^d - \tilde{\theta}_{ref}^d)$, $\tilde{\theta}_{ref}^d$ is the mean of $\tilde{\theta}_k^d$ in the window [k-5, k-20]. Since $g_{g,j}^d$ ranges from 0 to 1 and $(\tilde{\theta}_k^d - \tilde{\theta}_{ref}^d)$ is between -1 and 1, $\Omega$=1.5 is empirically selected to ensure that SI $\in$[0,1]. However, other values of $\Omega$ may be selected. FIG. 11C shows the SI values for all electrodes in δ frequency sub-bands for the MaxWC values depicted in FIG. 11B. FIG. 11C shows that SI values of multiple electrodes increase significantly at seizure onset (time 0).

The SI per electrode may be used to determine a significance of the electrode and the number of significant electrodes at 914. The number of electrodes that achieve statistically significant increase in SI during seizures may be a feature used to study the effects of VNS on EEG spatial synchronization. According to some implementations, this may be achieved by applying a one-sided robust statistical CUSUM procedure in the following recursive manner: Step 1. Calculate $\mu_{ref}^d(k,j)$ and $\sigma_{ref}^d(k,j)$ as the mean value and standard deviation of the SI calculated for the window [k-5, k-20] and $j^{th}$ electrode for sub-band d; Step. 2. Determine an adaptive threshold $\gamma_{k,j}^d$ as $$\gamma_{k,j}^d = \mu_{ref}^d(k,j) + 3\sigma_{ref}^d(k,j) \quad (11)$$

$$h_{k,j}^d = \alpha \Sigma_{p=k-M+1}^k \gamma_{p,j}^d \quad (12)$$

where 0≤α≤1; Step. 3 Estimate the CUSUM statistic recursively as:

$$U_{k,j}^d = \max\{0, (SI_{k,j}^d - \gamma_{k,j}^d) + U_{k-1,j}^d\} \quad (13)$$

Step 4. Identify the $j^{th}$ electrode for epoch k in sub-band d with statistically significant value of SI as:

$$\psi_{k,j}^d = \begin{cases} 1, & \text{if } U_{k,j}^d \geq h_{k,j}^d \\ 0, & \text{otherwise} \end{cases} \quad (14)$$

The number of electrodes that attain a significant value of SI across any of the sub-bands during the seizure may be used as the EEG-based feature to study the effects of closed-loop VNS, including the efficacy. If the electrodes are determined to contribute to the synchronization due to the seizure, they may be indicated as such for the physician at 916. If the electrodes are determined to not contribute to the synchronization due to the seizure, they may be indicated as such for the physician at 918.

The EEG-based data may be provided to the patient and/or physician in a variety of ways. For example, the electrodes may be overlaid on an MRI image of the patient with synchronized electrodes being displayed in one manner, while electrodes that do not contribute to the synchronization are displayed in a different manner. In some embodiments, the electrodes may by overlaid on a standard image of a head or brain instead of an image unique to the patient. In both cases, the electrodes may appear as different colors (e.g., red for synchronized and yellow for not synchronized) on a display for the physician. In another embodiment, different symbols may be used to represent synchronized and not synchronized electrode (e.g., solid circle for synchronized and open circle for not synchronized). In some embodiments, the code of the electrode, as labeled in FIGS. 4A and 4B, may be displayed to the physician in the form of a table, list, or chart differentiating between electrodes that contribute in synchronization and electrodes that do not contribute in synchronization. The shape and color selection is used as an example and is not intended to be limiting, and combination of colors, symbols, numbers, etc. may be used to differentiate between electrodes that contribute in synchronization and electrodes that do not contribute in synchronization. In other embodiments, the graphical data as seen in FIGS. 11A-11C may be provided. In some embodiments, graphical indications (e.g., text, colors, symbols, etc.) may be provided that provide a quantitative indication of synchronization for individual electrodes and/or for sets of electrodes based on the measurements determined for each electrode. In some embodiments, quantitative indication of synchronization may be shown for a comparison of a first seizure to a second seizure. For example, blue may be used to indicate no synchronization for a given electrode for both the first and second seizure, green may indicate a change from synchronization to no synchronization for a given electrode from the first seizure to the second seizure, yellow may indicate a synchronization for a given electrode for both the first and second seizure and red may indicate a change from no synchronization to synchronization for a given electrode from the first seizure to the second seizure. While four quantitative indications are described, any number of indications may be used. In addition, different shapes or symbols may be used instead of colors to differentiate the indications. In another embodiment, the quantitative indication of synchronization may be shown for a single seizure. For example, blue may be used to indicate no synchronization for a given electrode, green may indicate a low synchronization for a given electrode, yellow may indicate a moderate synchronization for a given electrode and red may indicate a high synchronization for a given electrode. While four quantitative indications are described, any number of indications may be used. Alternatively, instead of using distinct colors, a spectrum can be used that ranges from no synchronization to high synchronization. In addition, different shapes or symbols may be used instead of colors to differentiate the indications.

FIGS. 12A, 12C, 12E, and 12G are images of a wavelet coefficient change as a result of seizure before VNS therapy and FIGS. 12B, 12D, 12F and 12H are images of a wavelet coefficient change as a result of seizure after VNS therapy, according to an example embodiment. One patients is shown in each grouping (FIGS. 12A and 12B, FIGS. 12C and 12D, FIGS. 12E and 12F, and FIGS. 12G and 12H). The method followed to obtain these images is substantially similar to method 600 of FIG. 6, which may include method 900.

For each patient, the electrodes that attain a significant value of synchronizability index (SI) for most of seizures are defined as the ones that contributed the most to the ictal spatial synchronization. The maximum of wavelet coefficients (MaxWC) was calculated in a 450 sec time window (defined as seizure window), extending from 150 sec before the seizure annotation to 300 sec after the annotation and the mean value of the wavelet coefficients in a 100 sec preictal window that is immediately preceding the seizure window namely, $WC_{pre}$ for each of these electrodes. The change in each EEG electrode activity was calculated as $WC_{change}=MaxWC/WC_{pre}$. FIGS. 12A-12H demonstrate a $WC_{change}$ that is projected on scalp both prior and after VNS therapy using the standard 10-20 EEG system with 19 electrodes. $WC_{change}$ was calculated for the four frontal electrodes (F7, F3, F4, F8) along with five left electrodes (T3, T5, O1, C3, P3) and five right electrodes (T4, T6, O2, C4, P4). The anatomical location of these electrodes can be seen in FIGS. 4A-4B.

FIG. 13 is a table showing a summary of patients' characteristics for a study conducted relating to the methods described above. 51 patients (female (n=31, 60.78%), male (n=20, 39.22%), mean age of 37.69 (ranges 18-69), with the standard deviation of 13.67) were enrolled across two clinical trials (NCT01325623, NCT 01846741) wherein patients were implanted with an AspireSR® VNS Therapy System. Each subject participated in this study for a minimum of 5 weeks to include at least 1 week pre-implant, 2 weeks of post-implant recovery, one week of stimulation titration, and approximately 3 to 5 days of epilepsy monitoring unit (EMU) evaluation. At the beginning of the EMU visit, output current was increased to target level (at least 0.5 mA) that was tolerable for the patient and then the patient was set to the automated magnet mode (AMM) stimulation, which automatically delivers stimulation when a seizure associated with ictal tachycardia is detected. Concurrent EEG and ECG data was collected from all patients during the EMU evaluation. EEG data was recorded according to standard 10-20 system using 19 electrodes (in positions Fp1, Fp2, F7, F3, Fz, F4, F8, T7, C3, Cz, C4, T8, P7, P3, Pz, P4, P8, O1, O2) and the ECG are recorded via surface ECG electrodes. However, more or less electrodes could have been used. The sampling frequency was different from patient to patient with the range of 256 Hz to 2000 Hz.

In addition, for each patient, EEG and ECG data from a previous EMU visit that was prior to VNS implantation was also collected. These seizures will be referred to as "pre-treatment" seizures while the seizures that occurred in these patients following initiation of AMM-based VNS implantation will be called "post-treatment" seizures. 13 out of 51 patients were removed from this analysis because they either did not have EEG or ECG data for either the pre-treatment or post-treatment phase or had concurrent medication changes during the post-treatment phase and therefore may confound the evaluation of the true effect of the AMM-based VNS therapy.

Seizure annotations were provided by the clinical study sites following investigator review of both electrographic and clinical (video) data. Investigators were instructed to document the earliest seizure onset time indicated by the combination of the video and EEG input data. The number of annotated seizures in each patient both pre- and post-treatment are provided in FIG. 13. From FIG. 13, a total of 124 pre-treatment and 156 post-treatment seizures were analyzed in the study.

FIG. 14A is a graph displaying a magnitude and duration of a heart rate increase during a seizure before VNS therapy while FIG. 14B is a graph displaying a magnitude and duration of a heart rate increase during a seizure after VNS therapy. To evaluate the efficacy of the closed-loop VNS therapy in reducing ictal spatial synchronization (as measured by EEG-based feature) and the cardiac effects of seizures (as measured by ECG based features), the ECG- and EEG-feature extraction methods described above for determining 1) heart rate change ((in %), 2) duration of the heart rate change (in seconds), and 3) measure of spatial synchronization of EEG during a seizure were applied to the recorded EEG and ECG dataset from 38 patients (see FIG. 13). Seizures that occurred during automatic stimulation were compared to seizures that occurred prior to VNS therapy to evaluate if severity was reduced. FIGS. 14A and 14B present a representative example of the IHR versus time for Patient X pre- and post-treatment. FIG. 14A shows a HR change during a pre-treatment seizure to be 52.96% with the tachycardia duration of 163.57 sec. For the same patient, the value of HR change and tachycardia duration following VNS therapy is decreased to 8.57% and 82.31 sec respectively (see FIG. 14B), a substantial reduction of 44.39% in heart rate increase and 81.22 sec in tachycardia duration.

Figure 15A:
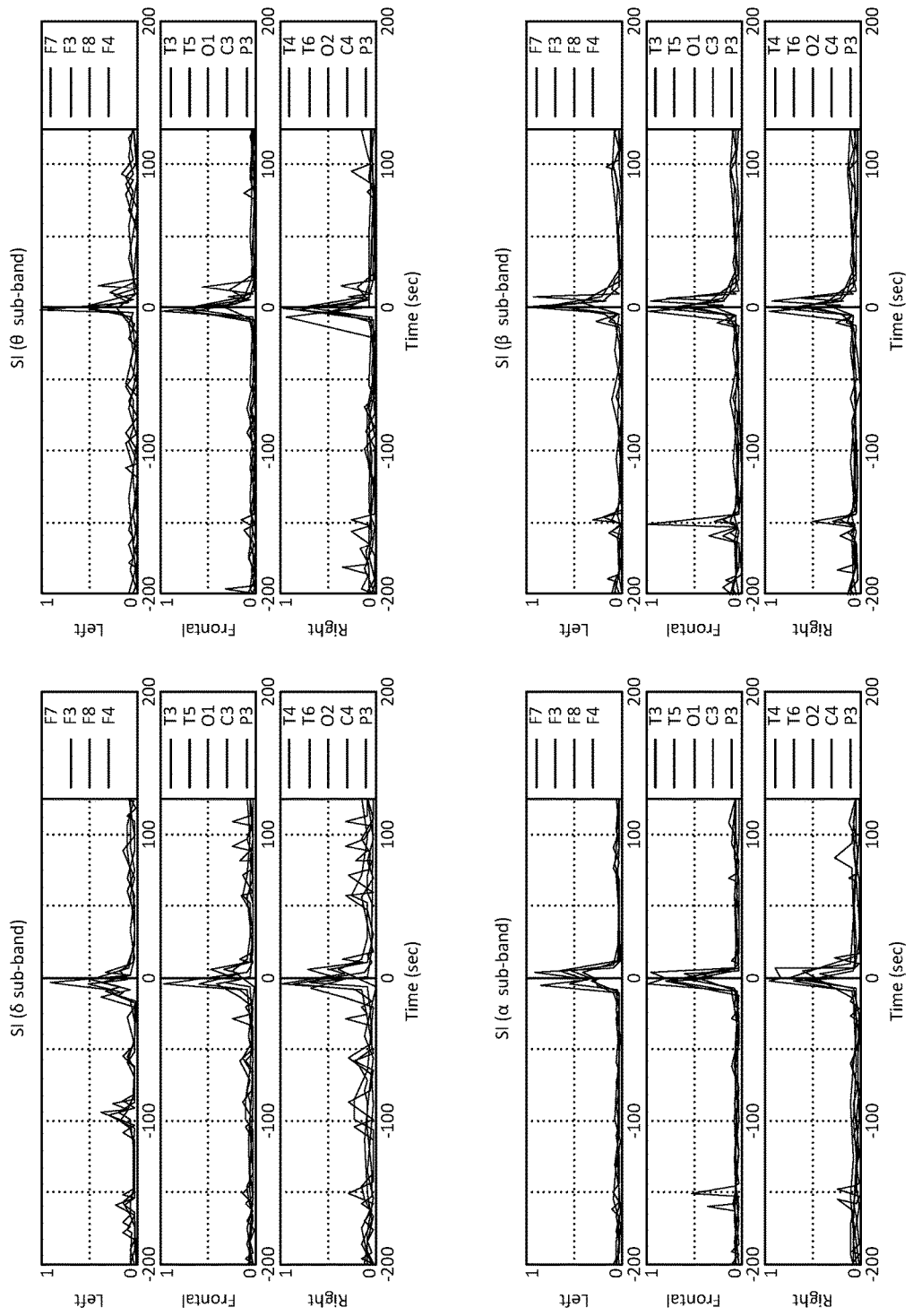
FIG. 15A is the synchronizability index for all frequency sub bands before VNS therapy, according to an example embodiment.
Figure 15B:
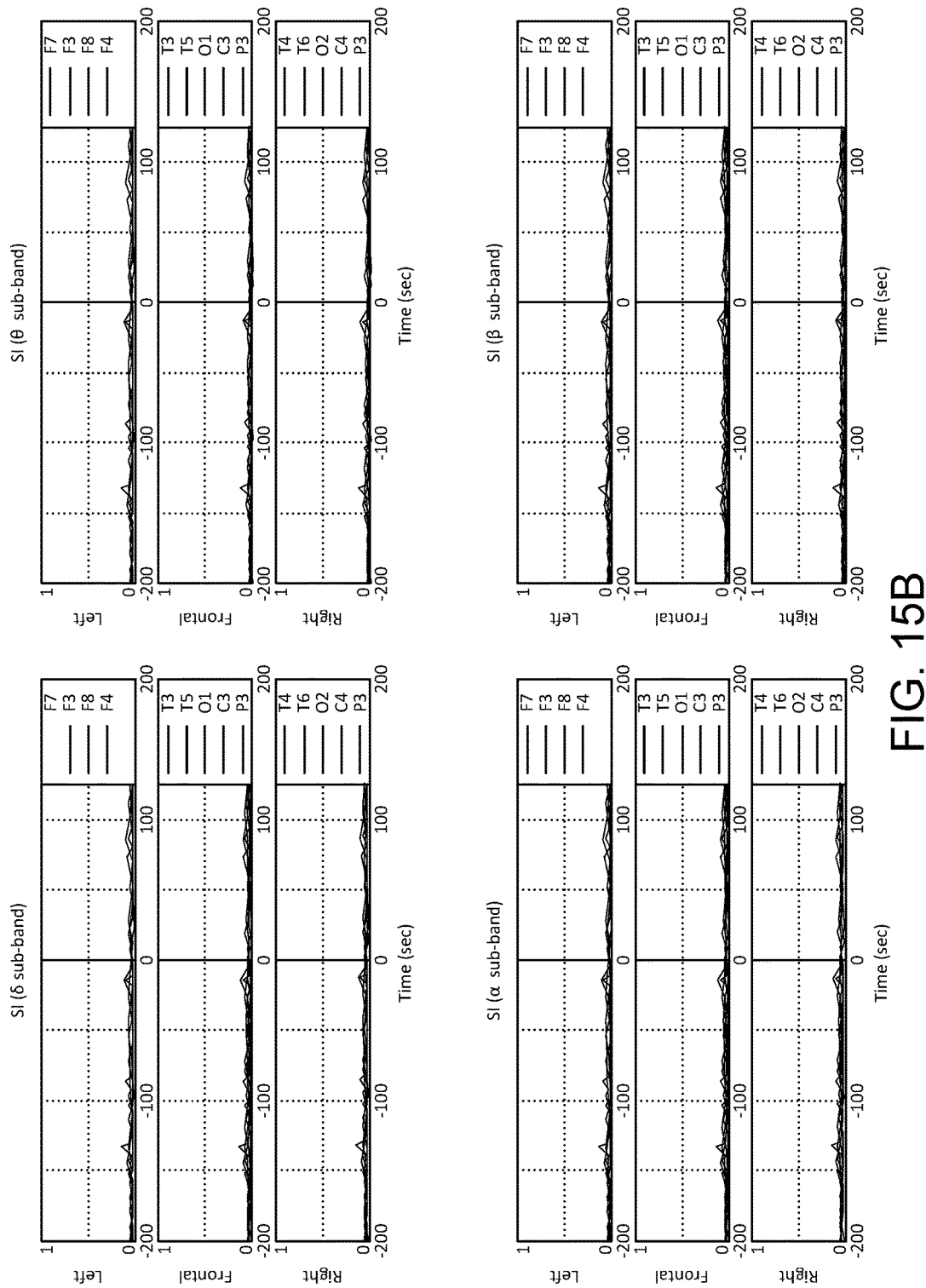
FIG. 15B is the synchronizability index for all frequency sub bands after VNS therapy, according to an example embodiment.

To demonstrate the effect of VNS therapy on EEG signals, FIGS. 15A and 15B shows the SI values for electrodes in four frequency sub-bands of $\delta$, $\theta$, $\alpha$ and $\beta$ for a pre-treatment (FIG. 15A) and post-treatment (FIG. 15B) seizure. From FIG. 15, it can be seen that the pre-treatment SI values are higher around seizure (time zero) in comparison to the pre-ictal SI values irrespective of the frequency band, suggesting an increase in the synchronizability of electrodes during seizure. Following treatment via closed-loop VNS therapy, the SI values decrease significantly for all electrodes suggesting a substantial reduction in synchronizability of the multiple EEG electrodes. This suggests that VNS therapy could effectively reduce the severity of brain activity caused by seizure in this patient. The overall performance of VNS therapy across all 38 patients using the three selected features of seizure severity is described below.

FIG. 16A is the synchronizability index for the $\delta$ frequency sub bands showing the synchronized electrodes during a seizure before VNS therapy while FIG. 16B is the synchronizability index for the $\delta$ frequency sub bands showing the synchronized electrodes during a seizure after VNS therapy, for a given patient. The synchronized electrodes during a seizure are designated by a filled in circle ("●"), while the electrodes that are determined to not be synchronized are designated with an open circle ("○"). When comparing the number and location of the synchronized electrodes of FIG. 16A ("pre-treatment") to the number and location of the synchronized electrodes of FIG. 16B ("post-treatment"), it can be seen that the number of synchronized electrodes decreased. However, FIGS. 16A and 16B show examples of the number and location of synchronized electrodes. The number and location of the synchronized electrodes may vary patient to patient and may vary seizure to seizure for a given patient. In addition, the number and location of the synchronized electrodes may vary based on the severity of the seizure, or the type of seizure.

Figure 17:
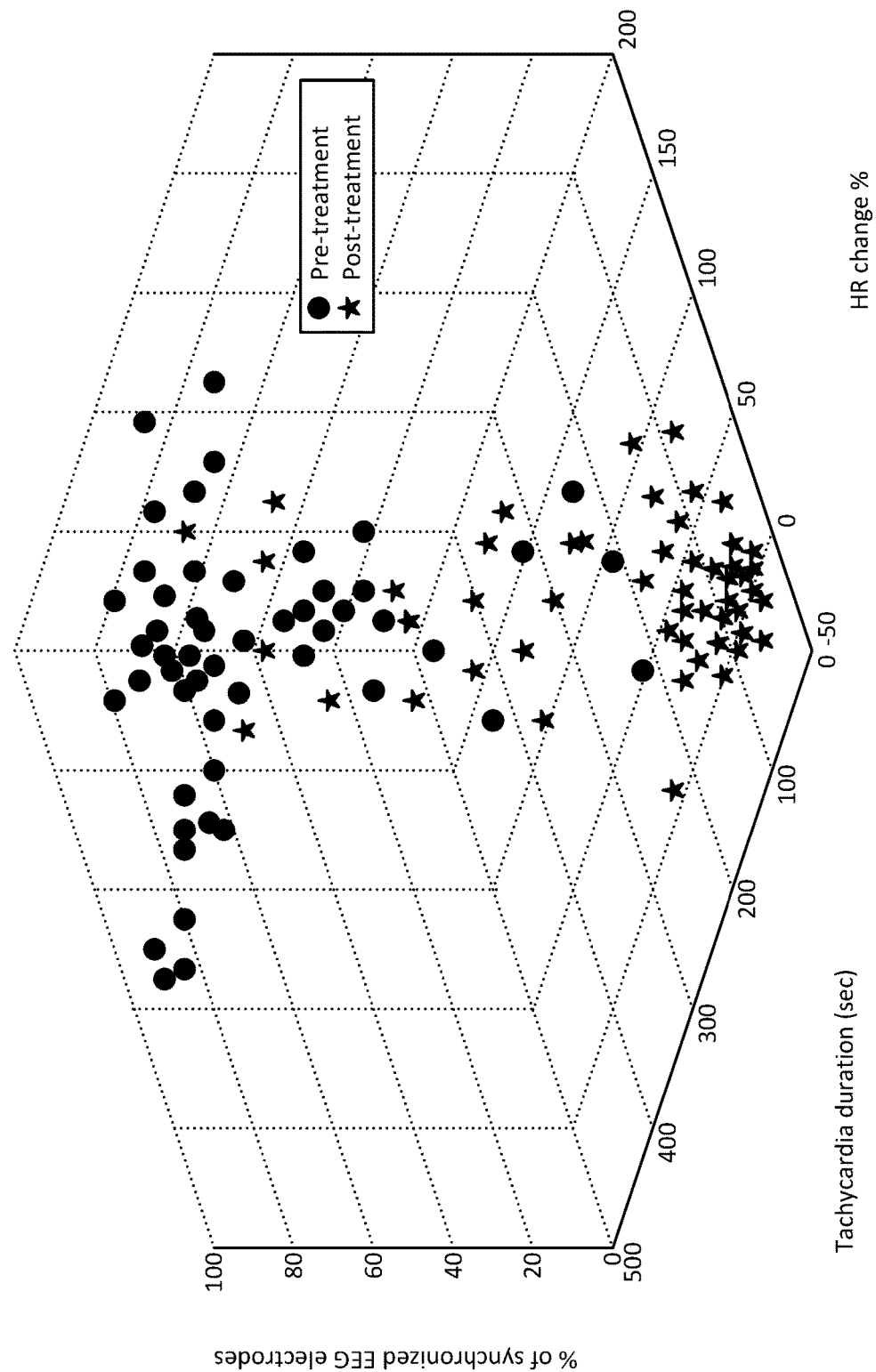
FIG. 17 is a three-dimensional view of a seizure severity feature space, according to an example embodiment.

FIG. 17 is a three-dimensional view of a seizure severity feature space, according to an example embodiment. A total of 280 seizures (124 pre-treatment and 156 post-treatment) were available for analysis (See FIG. 13). The three selected features per seizure and across all seizures was provided to a unsupervised Fuzzy-C-Mean classifier for clustering. This classifier divides these features into two clusters based on their hidden natural patterns and without considering their labels (pre- or post-treatment). Thus, the seizures in the same cluster are as similar as possible, while the seizures in different clusters are as dissimilar as possible. More specifically, the set of candidate ECG and EEG derived features namely 1) tachycardia HR change %, 2) tachycardia duration (sec), and 3) EEG electrodes that attain a high synchronizability index during a seizure, were estimated per seizure and across all seizures. All features were then normalized using their corresponding z-score value prior to input into the classifier.

Since the goal of the classification step in this analysis was to determine whether the selected features have significant discriminative power to correctly label seizures as being either from the group of pre-treatment or post-treatment, an unsupervised classifier was utilized. An advantage of unsupervised classifiers is that they do not utilize any training data for classification. Rather, this family of classifiers aggregates features into different classes based on the natural clusters that may exist in the feature values. Thus, if the selected features separate the seizures into two distinct classes of pre-treatment and post-treatment seizures, then it implies that the selected features have the ability to quantify the effectiveness of VNS therapy. In this study, the unsupervised Fuzzy-C-Mean (FCM) algorithm was used to implement the classifier. This algorithm is an iterative classification method that gives comparatively better than k-means algorithm for overlapped data set and can separate the two classes using least number of clusters. Results from the application of this procedure on the data are presented next. FIG. 17 depicts a three-dimensional feature space with the pre- and post-treatment seizures marked with circle and star markers respectively. This figure shows the ability of the classifier to cluster the seizures into two classes using the 3 selected features.

FIG. 18A is a table showing the statistical data as a result of the study performed. The mean value and standard deviation of the selected features of seizure severity across all seizures from the 38 patients before and after application of VNS therapy is shown, along with their corresponding t- and p-values. The t-statistic values in FIG. 18A were produced using a Welch t-test (which is the conventional student t-test generalized for unequal sample sizes and variances between the groups). From FIG. 18A, it appears that the mean value across all seizures and patients for each of the selected discriminating features is significantly lower ($p<0.05$) for post-VNS treatment compared to pre-VNS treatment. Overall, this suggests that each selected feature independently has the ability to statistically show the effect of VNS therapy on EEG synchronization and cardiac effects related to seizures. If there are significant correlations between selected features of severity, then the joint behavior of the features can be more discriminating than each feature taken individually. Therefore, the FCM classifier can be applied to evaluate the performance of VNS therapy using all there features in combination, as described herein.

FIG. 18B is a table showing the classification performance in predicting seizures according to the results of the study. Furthermore, FIG. 18B demonstrates that the classifier is capable of clustering pre- and post-treatment seizures with an accuracy of 83.57%. This indicates that the combination of selected features show the effect of VNS therapy in reducing ictal EEG synchronization and the magnitude and duration of heart rate increase. Furthermore, it appeared that 21 post-treatment seizures were mis-classified as pretreatment seizures. From these 21 post-treatment seizures, 11/21 seizures occurred in 5 patients (Patients 4, 9, 19, 24, 37 in FIG. 13), suggesting that the application of VNS therapy did not have an effect of the seizures of these patients. In the remaining 10/21 misclassified seizures, there was a reduction to a lower value in all the 3 selected features, however, the change was not statistically significant ($p>0.05$). Also, 25 pre-treatment seizures were mis-classified as post-treatment seizures. Further review of the EEG confirmed that 18/25 seizures appeared to be psychogenic non-epileptic events and the remaining 7/25 seizures had higher values in all 3 selected features, however, they were not statistically significant ($p>0.05$).

FIG. 18C is a table showing the classification of seizures that received VNS therapy according to the results of the study. Specifically, the ability of the classifier to discriminate the seizures that received acute responsive VNS therapy (as verified using the AspireSR device log files) from the pre-treatment ones was analyzed. Using this definition, 70 out of 156 post-treated seizures were considered for this meta-analysis. The corresponding classification performance is shown in FIG. 18C. The classifier is again capable of discriminating the two classes with an accuracy of 79.90%, where the misclassified post-treatment seizures are the same as the ones noted in FIG. 18B. This finding suggests that VNS therapy could also be able to acutely effect the severity of seizures.

In summary, this study proposed a method to determine the effectiveness of VNS therapy in reducing the severity of the seizures in epileptic patients from their EEG and ECG signals around the seizure annotation. Two data sets that were collected from 13 European sites and 10 US sites are used to build a classifier, which determines if the seizure happens before or during the VNS therapy. The process consists of the following two components: feature extraction and classification procedure. In this study, a set of 3 "discriminating features", the heart rate change %, tachycardia duration, and affected electrodes due to the seizure was identified that could distinguish the severity of the seizures pre- and post-treatment in a group of 29 subjects who were under VNS therapy. The unsupervised FCM classifier was used. The unsupervised approach may be preferable to the supervised one in areas of complex topography. In such conditions, selecting the training data set is usually difficult in supervised approach because of the variability of spectral responses within each class. Consequently, an appropriate training data collection can be very hard and time consuming. Conversely, spectrally distinguishable classes could be classified by the unsupervised approach accurately.

The selected discriminating features found to be able to distinguish 1) all pre-treatment seizures from post-treatment ones and 2) the acute post-treatment seizures with the HR change % of above 20% from pre-treatment ones. In both cases the Fuzzy C-mean classifiers show more than 80% performance. The findings suggest that combining EEG and ECG signals with clustering techniques may provide insights into the therapeutic effect of VNS therapy.

In view of the above, EEG synchronization data may be used to evaluate the effectiveness of VNS therapy in reducing seizure severity in patients with epilepsy. To quantify the severity of each seizure, three features may be extracted: (1) heart rate change (in %) during a seizure, (2) duration of the heart rate change (in seconds), and (3) measure of spatial synchronization of EEG during a seizure. These features may be used to manage and/or adjust the automated delivery of VNS Therapy to a patient based on seizure detection, and may further be used to configure therapy to evaluate and reduce seizure severity. This analysis technique and the embodiments utilizing this technique may provide an objective quantification of the effects of closed-loop neuromodulation. Furthermore, the evaluation of VNS Therapy using dynamical analysis of EEG-ECG data may provide insights into the mechanism of action of this therapy on seizures as well as on the associated co-morbidities.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z. Thus, such conjunctive language is not generally intended to imply that certain embodiments require at least one of X, at least one of Y, and at least one of Z to each be present.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of detecting an improvement in a seizure condition of a patient, the method comprising:
   identifying a first EEG synchronization of a first seizure of the patient;
   applying a therapy configured to improve the seizure condition of the patient;
   identifying a second EEG synchronization of a second seizure of the patient subsequent to application of the therapy, wherein an improvement of the seizure condition of the patient is demonstrated by a reduced EEG synchronization of the patient such that the second EEG synchronization is less than the first EEG synchronization; and
   modifying the therapy based on at least one of the second EEG synchronization or a comparison of the first and second EEG synchronization.

2. The method of claim 1, wherein the therapy is at least one of a vagus nerve stimulation therapy or a drug therapy.

3. The method of claim 1, further comprising:
   identifying a first amount of heart rate increase of the seizure condition of the patient;
   identifying a second amount of heart rate increase of the seizure condition of the patient subsequent to application of the therapy, wherein an improvement of the seizure condition of the patient is demonstrated by a reduced increase in heart rate of the patient wherein the second amount of heart rate increase is less than the first amount of heart rate increase.

4. The method of claim 1, further comprising:
   identifying a first duration of increased heart rate of the seizure condition of the patient;
   identifying a second duration of increased heart rate of the seizure condition of the patient subsequent to application of the therapy, wherein an improvement of the seizure condition of the patient is demonstrated by a reduced duration of increased heart rate wherein the second duration of increased heart rate is less than the first duration of increased heart rate.

5. The method of claim 1, wherein the first and second EEG synchronization are determined for a plurality of EEG sensors and a plurality of frequency bands for each of the plurality of EEG sensors.

6. The method of claim 1, wherein identifying the first EEG synchronization and identifying the second EEG synchronization each comprise:
   extracting maximum wavelet coefficients in a plurality of epochs and a plurality of frequency bands for a plurality of EEG sensors;
   computing a global spatial synchronization for each frequency band across the plurality of EEG sensors using the maximum wavelet coefficients; and
   estimating a synchronizability index for each of the plurality of EEG sensors using the global spatial synchronization.

7. The method of claim 6, further comprising, for each of the plurality of EEG sensors, classifying the EEG sensors as contributing to synchronization in response to determining a significance for each of the plurality of EEG sensors based on the synchronizability index, wherein the significance indicates an increase in the sychronizability index during the seizure.

8. The method of claim 7, further comprising determining a number of EEG sensors contributing to seizure from the plurality of EEG sensors based on the significance for each of the plurality of EEG sensors.

9. The method of claim 8, further comprising evaluating an efficacy of treatment by comparing the number of EEG sensors contributing to seizure in the first EEG synchronization to the number of EEG sensors contributing to seizure in the second EEG synchronization.

10. The method of claim 1, further comprising providing a visual representation of at least one of the first EEG synchronization, the second EEG synchronization, or a comparison of the first and second EEG synchronization to at least one of the patient or a physician.

11. The method of claim 1, further comprising generating an indication of an efficacy of the therapy using at least one of the second EEG synchronization or the comparison of the second EEG synchronization to the first EEG synchronization.

12. A device configured to detect an improvement in a seizure condition of a patient, the device comprising:
   at least one EEG sensor configured to generate EEG data; and
   a therapy analysis device configured to receive the EEG data,
   wherein the therapy analysis device is configured to evaluate an effect of a therapy, the evaluation comprising:
   identifying a first EEG synchronization of the seizure condition of the patient;
   applying a therapy configured to improve the seizure condition of the patient;
   identifying a second EEG synchronization of the seizure condition of the patient subsequent to application of the therapy, wherein an improvement of the seizure condition of the patient is demonstrated by a reduced EEG synchronization of the patient such that the second EEG synchronization is less than the first EEG synchronization; and
   modifying the therapy based on at least one of the second EEG synchronization or a comparison of the first and second EEG synchronization.

13. The device of claim 12, wherein the therapy is at least one of a vagus nerve stimulation therapy or a drug therapy.

14. The device of claim 12, further comprising at least one heart rate sensor.

15. The device of claim 14, wherein the evaluation further comprises:
   identifying a first amount of heart rate increase of the seizure condition of the patient;
   identifying a second amount of heart rate increase of the seizure condition of the patient subsequent to application of the therapy, wherein an improvement of the seizure condition of the patient is demonstrated by a reduced increase in heart rate of the patient wherein the second amount of heart rate increase is less than the first amount of heart rate increase.

16. The device of claim 14, wherein the evaluation further comprises:
   identifying a first duration of increased heart rate of the seizure condition of the patient;
   identifying a second duration of increased heart rate of the seizure condition of the patient subsequent to application of the therapy, wherein an improvement of the seizure condition of the patient is demonstrated by a reduced duration of increased heart rate wherein the second duration of increased heart rate is less than the first duration of increased heart rate.

17. The device of claim 12, wherein the first and second EEG synchronization are determined for the at least one EEG sensor and a plurality of frequency bands for the at least one EEG sensor.

18. The device of claim 12, wherein identifying the first EEG synchronization and identifying the second EEG synchronization each comprise:
   extracting maximum wavelet coefficients in a plurality of epochs and a plurality of frequency bands for a plurality of EEG sensors;
   computing a global spatial synchronization for each frequency band across the plurality of EEG sensors using the maximum wavelet coefficients; and
   estimating a synchronizability index for each of the plurality of EEG sensors using the global spatial synchronization.

19. The device of claim 18, wherein identifying the first EEG synchronization and identifying the second EEG synchronization each further comprises, for each of the plurality of EEG sensors, classifying the EEG sensors as contributing to synchronization in response to determining a significance for each of the plurality of EEG sensors based on the synchronizability index, wherein the significance indicates an increase in the sychronizability index during the seizure.

20. The device of claim 19, wherein identifying the first EEG synchronization and identifying the second EEG synchronization each further comprises determining a number of EEG sensors contributing to seizure from the plurality of EEG sensors based on the significance for each of the plurality of EEG sensors.

21. The device of claim 20, the therapy analysis device is further configured to evaluate the effect of a therapy by comparing the number of EEG sensors contributing to seizure in the first EEG synchronization to the number of EEG sensors contributing to seizure in the second EEG synchronization.

22. The device of claim 12, the therapy analysis device is further configured to provide a visual representation of at least one of the first EEG synchronization, the second EEG synchronization, or a comparison of the first and second EEG synchronization to at least one of the patient or a physician.

23. The device of claim 12, wherein the therapy analysis device is configured to generate an indication of an efficacy of the therapy using at least one of the second EEG synchronization or the comparison of the second EEG synchronization to the first EEG synchronization.

24. A method of detecting an improvement in a seizure condition of a patient, the method comprising:
   identifying a first EEG synchronization of the seizure condition of the patient by:
      extracting first maximum wavelet coefficients in a first plurality of epochs and a plurality of frequency bands for a plurality of EEG sensors;
      computing a first global spatial synchronization for each frequency band across the plurality of EEG sensors using the first maximum wavelet coefficients; and
      estimating a first synchronizability index for each of the plurality of EEG sensors using the first global spatial synchronization;
   applying stimulation to a vagus nerve of the patient using a vagus nerve stimulation device configured to improve the seizure condition of the patient;
   identifying a second EEG synchronization of the seizure condition of the patient subsequent to application of the stimulation by:
      extracting second maximum wavelet coefficients in a second plurality of epochs and the plurality of frequency bands for the plurality of EEG sensors;
      computing a second global spatial synchronization for each frequency band across the plurality of EEG sensors using the second maximum wavelet coefficients; and
      estimating a second synchronizability index for each of the plurality of EEG sensors using the second global spatial synchronization; and
   generating an indication of an efficacy of the stimulation to the vagus nerve using at least one of the second synchronizability index or a comparison of the second synchronizability index to the first synchronizability index.

25. The method of claim 24, further comprising:
   identifying a first amount of heart rate increase of the seizure condition of the patient;
   identifying a second amount of heart rate increase of the seizure condition of the patient subsequent to application of the therapy, wherein an improvement of the seizure condition of the patient is demonstrated by a reduced increase in heart rate of the patient wherein the second amount of heart rate increase is less than the first amount of heart rate increase.

26. The method of claim 24, further comprising:
   identifying a first duration of increased heart rate of the seizure condition of the patient;
   identifying a second duration of increased heart rate of the seizure condition of the patient subsequent to application of the therapy, wherein an improvement of the seizure condition of the patient is demonstrated by a reduced duration of increased heart rate wherein the second duration of increased heart rate is less than the first duration of increased heart rate.

27. The method of claim 24, further comprising for each of the plurality of EEG sensors, classifying the EEG sensors as contributing to synchronization in response to determining a first significance for each of the plurality of EEG sensors based on the first synchronizability index and determining a second significance for each of the plurality of EEG sensors based on the second synchronizability index, wherein the first and second significance indicate a statistically significant increase in the first and second sychronizability index, respectively, during the seizure.

28. The method of claim 27, further comprising determining a first number of EEG sensors contributing to seizure from the plurality of EEG sensors based on the first significance for each of the plurality of EEG sensors and a second number of EEG sensors contributing to seizure from the plurality of EEG sensors based on the second significance for each of the plurality of EEG sensors.

29. The method of claim 28, further comprising evaluating an efficacy of treatment by comparing the first number of EEG sensors contributing to seizure in the first EEG synchronization to the second number of EEG sensors contributing to seizure in the second EEG synchronization.

30. The method of claim 24, further comprising modifying the therapy based on at least one of the second EEG synchronization or a comparison of the first and second EEG synchronization.

31. The method of claim 24, further comprising providing a visual representation of at least one of the first EEG synchronization, the second EEG synchronization, or a comparison of the first and second EEG synchronization to at least one of the patient or a physician.

* * * * *